United States Patent
Gestrelius et al.

(10) Patent No.: US 7,294,352 B2
(45) Date of Patent: Nov. 13, 2007

(54) MATRIX PROTEIN COMPOSITION FOR TREATING INFLAMMATION

(75) Inventors: Stina Gestrelius, Lund (SE); Lars Hammarström, Djursholm (SE); Petter Lyngstadaas, Nesoddtangen (NO); Christer Andersson, Vellinge (SE); Ivan Slaby, Malmo (SE); Tomas Hammargren, Malmo (SE)

(73) Assignee: Biora BioEx AB, Malmo (SE)

( * ) Notice: Subject to any disclaimer, the term of this patent is extended or adjusted under 35 U.S.C. 154(b) by 597 days.

(21) Appl. No.: 10/698,618

(22) Filed: Oct. 30, 2003

(65) Prior Publication Data

US 2005/0271604 A1    Dec. 8, 2005

Related U.S. Application Data

(62) Division of application No. 10/156,300, filed on May 28, 2002, now Pat. No. 6,720,009, which is a division of application No. 09/258,613, filed on Feb. 26, 1999, now Pat. No. 6,503,539.

(60) Provisional application No. 60/081,551, filed on Apr. 13, 1998.

(30) Foreign Application Priority Data

Feb. 27, 1998 (DK) .................... 0270/98
Oct. 16, 1998 (DK) ................ 1998 01328

(51) Int. Cl.
*A61K 35/32*    (2006.01)
(52) U.S. Cl. ..................................... 424/549
(58) Field of Classification Search .............. None
See application file for complete search history.

(56) References Cited

U.S. PATENT DOCUMENTS 5,071,958 A * 12/1991 Hammarstrom et al. .... 530/344

OTHER PUBLICATIONS

"infection." The American Heritage® Stedman's Medical Dictionary. Houghton Mifflin Company. Sep. 6, 2006. <Dictionary.com http://dictionary.reference.com/search?q=infection>.*

* cited by examiner

*Primary Examiner*—L. Blaine Lankford, Jr.
*Assistant Examiner*—Allison M. Ford
(74) *Attorney, Agent, or Firm*—Rissman Jobse Hendricks & Oliverio LLP

(57) ABSTRACT

Active enamel substances may be used for the preparation of a pharmaceutical or cosmetic composition for healing of a wound, improving healing of a wound, soft tissue regeneration or repair, or for preventing or treating infection or inflammation.

18 Claims, 12 Drawing Sheets

| FIG. 3A |
| FIG. 3B |

MATRIX PROTEIN COMPOSITION FOR TREATING INFLAMMATION

RELATED APPLICATIONS

This application claims priority to U.S. patent application Ser. No. 10/156,300 filed May 28, 2002, now U.S. Pat. No. 6,720,009, which is a Divisional of U.S. patent application Ser. No. 09/258,6 13, filed Feb. 26, 1999, now U.S. Pat. No. 6,503,539, which is a continuation-in-part of U.S. Provisional Application 60/081,551, filed Apr. 13, 1998. The entireties of these applications are incorporated herein by reference.

FIELD OF THE INVENTION

The present invention relates to the uses of enamel matrix, enamel matrix derivatives and/or enamel matrix proteins as therapeutic or prophylactic agents. The substances are active as wound healing, anti-bacterial and/or anti-inflammatory agents.

BACKGROUND OF THE INVENTION

Enamel matrix proteins such as those present in enamel matrix are most well-known as precursors to enamel. Enamel proteins and enamel matrix derivatives have previously been described in the patent literature to induce hard tissue formation (i.e. enamel formation, U.S. Pat. No. 4,672,032 (Slavkin)) or binding between hard tissues (EP-B-0 337 967 and EP-B-0 263 086). Thus, the prior art is solely centred on regeneration of hard tissues, while the present application deals with beneficial effects on soft tissue wound healing and anti-bacterial and anti-inflammatory effects which are unexpected findings.

DISCLOSURE OF THE INVENTION

The present invention is based on the finding that enamel matrix, enamel matrix derivatives and/or enamel matrix proteins (the term "an active enamel substance" is in the following also used for an enamel matrix, an enamel matrix derivative or an enamel matrix protein) are beneficial agents for the enhancement or improvement of the healing of wounds in soft tissues (i.e. non-mineralised tissues) such as collagen or epithelium containing tissues, including skin and mucosa, muscle, blood and lymph vessels, nerve tissues, glands, tendons, eyes and cartilage. As demonstrated in the experimental section herein, the enamel matrix, enamel matrix derivatives and/or enamel matrix proteins exert especially useful effects in the healing or prophylaxis of soft tissue wounds.

Accordingly, the invention relates to the use of a preparation of an active enamel substance for the preparation of a pharmaceutical or cosmetic composition i) for healing of a wound, ii) for improving healing of a wound, and/or iii) for soft tissue regeneration and/or repair.

In another aspect, the invention relates to a method of improving the healing of a wound or of promoting soft tissue regeneration and/or repair, the method comprising administering, to an individual in need thereof, a therapeutically or prophylactically effective amount of an active enamel substance.

Furthermore, enamel matrix, enamel matrix derivatives and enamel matrix proteins have been found to have anti-bacterial and/or anti-inflammatory properties that can be used for treatment of both soft and hard (i.e. mineralised) tissue conditions.

In other aspects the invention relate to the use of a preparation of an active enamel substance for the preparation of a pharmaceutical composition for the prevention and/or treatment of an infection or an inflammatory condition.

Wound Healing

Wounds and/or ulcers are normally found protruding from the skin or on a mucosal surface or as a result of an infarction in an organ ("stroke"). A wound may be a result of a soft tissue defect or a lesion or of an underlying condition. Regeneration of experimentally provoked periodontal wounds has previously been described by the inventors and is not intended to be within the scope of the present invention. In the present context the term "skin" relates to the outermost surface of the body of an animal including a human and embraces intact or almost intact skin as well as an injured skin surface. The term "mucosa" relates to undamaged or damaged mucosa of an animal such as a human and may be the oral, buccal, aural, nasal, lung, eye, gastrointestinal, vaginal, or rectal mucosa.

In the present context the term "wound" denotes a bodily injury with disruption of the normal integrity of tissue structures. The term is also intended to encompass the terms "sore", "lesion", "necrosis" and "ulcer". Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions.

The term "wound" used in the present context denotes any wound (see below for a classification of wounds) and at any particular stage in the healing process including the stage before any healing has initiated or even before a specific wound like a surgical incision is made (prophylactic treatment).

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore as mentioned above, in the present context the term "wound" encompasses the term "ulcer", "lesion", "sore" and "infarction", and the terms are indiscriminately used unless otherwise indicated.

The kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

The healing effect of an active enamel substance has been found to be of interest in connection with wounds which are present in the oral cavity. Such wounds may be bodily injuries or trauma associated with oral surgery including periodontal surgery, tooth extraction(s), endodontic treatment, insertion of tooth implants, application and use of tooth prothesis, and the like. In the experimental section herein the beneficial effect of an active enamel substance on such wounds has been demonstrated. Furthermore, a soft tissue healing effect has been observed.

In the oral cavity healing of wounds like aphthous wounds, traumatic wounds or herpes associated wounds is also improved after application of an active enamel substance. The traumatic wounds and the herpes associated wounds can of course also be situated on other parts of the body than in the oral cavity.

In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

Ischemic ulcers and pressure sores are wounds which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and—in those cases where the skin surface is more or less injured—also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process whereby the architecture and function of lost tissue are completely renewed. Repair, on the other hand, is a biological process whereby continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process which is almost always involved is the formation of a transient connective tissue in the area of tissue injury. This process starts by formation of a new extracellular collagen matrix by fibroblasts. This new extracellular collagen matrix is then the support for a connective tissue during the final healing process. The final healing is, in most tissues, a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing can be very slow and the wound may persist for an extended period of time, i.e. months or even years.

The stages of wound healing normally include inflammation (normally 1-3 days), migration (normally 1-6 days), proliferation (normally 3-24 days) and maturation (normally 1-12 months). The healing process is a complex and well orchestrated physiological process that involves migration, proliferation and differentiation of a variety of cell types as well as synthesis of matrix components. The healing process may be separated into the following three phases:

i) Haemostasis and Inflammation

When platelets are present outside the circulatory system and exposed to thrombin and collagen, they become activated and they aggregate. Thus, platelets initiate the repair process by aggregating and forming a temporary plug to ensure haemostasis and prevent invasion from bacteria. The activated platelets initiate the coagulation system and release growth factors like platelet-derived growth factor (PDGF) and epidermal growth factors (EGFs) and transforming growth factors (TGFs).

The first cells to invade the wound area are neutrophils followed by monocytes which are activated by macrophages.

The major role of neutrophils appears to be clearing the wound of or defending the wound against contaminating bacteria and to improve the healing of the wound by removing dead cells and platelets. The infiltration of neutrophils ceases within about the first 48 hours provided that no bacterial contamination is present in the wound. Excess neutrophils are phagocytosed by tissue macrophages recruited from the circulating pool of blood-borne monocytes. Macrophages are believed to be essential for efficient wound healing in that they also are responsible for phagocytosis of pathogenic organisms and a clearing up of tissue debris. Furthermore, they release numerous factors involved in subsequent events of the healing process. The macrophages attract fibroblasts which start the production of collagen.

ii) Granulation Tissue Formation and Re-Epithelization

Within 48 hours after wounding, fibroblasts begin to proliferate and migrate into the wound space from the connective tissue at the wound edge. The fibroblasts produce collagens and glycosaminoglycans and inter alia low oxygen tension at the wound stimulates proliferation of endothelial cells. The endothelial cells give rise to the formation of a new capillary network.

Collagenases and plasminogen activators are secreted from keratinocytes. If the wound is left undisturbed and well-nourished with oxygen and nutrients, keratinocytes will migrate over the wound. Keratinocytes are believed only to migrate over viable tissue and, accordingly, the keratinocytes migrate into the area below the dead tissue and the crust of the wound.

The wound area is further decreased by contraction.

iii) Dermal Remodelling

As soon as the re-epithelization is completed the remodelling of the tissue begins. This phase, which lasts for several years, restores the strength to the wounded tissue.

All of the above-mentioned healing processes take considerable time. The rate of healing is influenced by the wound's freedom from infection, the general health of the individual, presence of foreign bodies, etc. Some pathologic conditions like infection, maceration, dehydration, generally poor health and malnutrition can lead to formation of a chronic ulcer such as, e.g., ischemic ulcers.

Until at least superficial healing has occurred, the wound remains at risk of continued or new infection. Therefore, the quicker the wound can heal, the sooner the risk is removed.

Thus, any procedure that can influence the rate of wound healing or favourably influence the healing of wounds is of great value.

Furthermore, as almost all tissue repair processes include the early connective tissue formation, a stimulation of this and the subsequent processes are contemplated to improve tissue healing.

In the present context the term "clinical healing" is used to denote a situation where no tissue interruption can be visually observed and only discrete signs of inflammation are present such as a light redness or a discretely swollen tissue. In addition, no complaints of pain are present when the organ is relaxed or untouched.

As mentioned above, the invention relates to the use of enamel matrix, enamel matrix derivatives and/or enamel matrix proteins as a wound healing agent, i.e. an agent which accelerates, stimulates or promotes healing of dermal or mucosal wounds. Accordingly, an important use is also the use as tissue regeneration and/or repair agents. Furthermore, due to the wound healing effect, enamel matrix, enamel matrix derivatives and/or enamel matrix proteins have pain relief effect.

Traditionally, dry or wet-to-dry dressings have been most commonly used for wound care. These are gradually being replaced by moist environments using occlusive dressings.

To successfully repair or replace a failed body part, the processes of wound healing, fibrosis and microbial invasion must be balanced against each other. Many tools available to ward off infection compromise wound healing. Delayed wound healing or inflammation can exacerbate fibrosis. Moreover, it has previously been suggested that growth factors like epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2) are conductors of the wound healing process and they are frequently cited as promoters of wound healing; however, they can actually promote fibrosis which in turn may impair successful healing. Even though accelerated healing offers the most promise for reducing the risk of infection and the resulting inflammation that can lead to scar formation, therapeutic attempts to accelerate the normal wound healing process have met with relatively little success. This is likely because the repair process involves the concerted involvement of a number of factors, cf. above.

To this end, the present inventors have observed that in various cell cultures of fibroblasts (embryonal, dermal, derived from the periodontal ligament, fish or bird), twice as much TGFβ1 is produced in the cell cultures stimulated with EMDOGAIN®(from BIORA AB, S-205 12 Malmö, Sweden containing 30 mg freeze-dried Enamel Matrix protein (in the following abbreviated to EMD) and 1 ml Vehicle Solution (Propylene Glycol Alginate), which are mixed prior to application, unless the protein and the Vehicle are tested separately, the weight ratio being about 85/5/10 between the main protein peaks at 20, 14 and 5 kDa, respectively) compared to non-stimulated cultures when assayed by, e.g., ELISA in a sample from the culture medium (vide Example 1 below). The increase is present after 24 hours of culture, but more pronounced on the following days (days 2 and 3). After the second day, also the cell proliferation is increased in cell cultures stimulated with EMDOGAIN®. A similar but less pronounced increase of TGFβ1 production is observed in human epithelial cells. As TGFβ1 seems to be of central importance in the epithelisation of surface wounds, these findings support the concept of the present invention.

In the oral cavity the use of dressings is common. Such dressings are of the traditional type, e.g. Surgipads to stop bleeding and Coe-Pack periodontal dressing (Coe Laboratories, the GC Group, Chicago, USA) on open wounds, Gaze drenched in antibiotic solution is inserted in tooth extraction alveoli and requires removal after a few days when the healing has started. Rinsing with antiseptics such as chlorhexidine is regularly used after oral surgery. Sometimes general or topical antibiotics are also prescribed.

In general specific precautions have to be taken into considerations in connection with treatment of wounds, such as, e.g., sterility considerations, contamination problems, correct application of bandages/dressings etc. which normally require that the treatment/application is performed by well-educated nurses or the like. Thus, wound treatment often becomes a very expensive operation when the wound healing agent is to be applied several times daily. A desired reduction in the costs involved in wound healing treatment is therefore obtainable when the application frequency can be reduced or if the healing processes are improved leading to a reduction in the time period required to heal the wound.

The present inventors have now found that enamel matrix, enamel matrix derivatives and/or enamel matrix proteins have wound healing properties. Furthermore, there are indications of that the application of enamel matrix, enamel matrix derivatives and/or enamel matrix proteins lead to improved wound healing. Especially, the inventors have observed that after application of enamel matrix proteins and/or enamel matrix derivatives, the inflammation stage is shortened and the typical signs such as warmth, redness, oedema and pain are less noticeable, and new tissues are formed more rapidly. The observed time for wound healing (e.g. after surgery) is significantly shortened as compared to surgery without the use of enamel matrix, enamel matrix derivatives and/or enamel matrix proteins.

The therapeutic and/or prophylactic activity of enamel matrix, enamel matrix derivatives and/or enamel matrix proteins may of course be evidenced by in vivo tests using experimental animals or humans (cf. the experimental section herein). However, an indication of the efficacy and/or activity of enamel matrix, enamel matrix derivatives and/or enamel matrix proteins can be obtained by performing relatively simple in vitro tests such as, e.g., tests involving cell cultures.

Furthermore, there are several parameters which may be employed in order to evaluate a wound healing effect. These include:

Computer aided planimetry (evaluation of rate of open wound healing)
Laser doppler imaging (evaluation of wound perfusion)
Tensiometry (evaluation of wound strength)
Histopathology/cytology (microscopic evaluation of wound tissues and fluids)
Biochemistry (HPLC/RIA) (evaluation of various drugs and biochemical components of tissue healing)
Electrodiagnostics (evaluation of relationship of wound healing and innervation)
Scintigraphy (radionuclide imaging of wound tissue)

In connection with treatment of wounds/ulcers, debridement and wound cleansing are of particular importance. It is believed that the cleaning and/or debridement of wounds/ulcers are a prerequisite for the healing process and, furthermore, when wound healing agents are applied such agents have to exert their effect on fresh and vital tissue and not on dead tissue or contaminated tissue. Debridement of necrotic tissue can be performed by at least four different methods: i) sharp debridement, ii) mechanical debridement, iii) enzymatic debridement, and iv) autolytic debridement.

Therefore, the present invention relates also to the use of a debridement method in combination with the use of enamel matrix, enamel matrix derivatives and/or enamel matrix proteins for the healing or prevention of wounds. Such combination therapy involves the following two steps, namely i) a debridement method and ii) application of an enamel matrix, enamel matrix derivatives and/or enamel matrix proteins and the two steps may be carried out as many times as desired and in any suitable order.

When the wound has been subjected to debridement, the enamel matrix, enamel matrix derivatives and/or enamel matrix proteins may be applied either directly on or into the wound or it can be applied in the form of any suitable pharmaceutical composition such as, e.g., a dry or moist, clean dressing into which the enamel matrix, enamel matrix derivatives and/or enamel matrix proteins has been incorporated. The enamel matrix, enamel matrix derivatives and/or enamel matrix proteins may of course also be applied in connection with cleansing of the wound.

As will be discussed later, the enamel matrix, enamel matrix derivatives and/or the enamel matrix proteins may be used as such or they may be used in a suitable preparation or pharmaceutical composition.

Infection-Decreasing Effect

In a further aspect of the present invention, the enamel matrix, enamel matrix derivatives and/or enamel matrix proteins are used as therapeutic or prophylactic agents having an anti-microbial effect. The enamel matrix, enamel matrix derivatives and/or enamel matrix proteins exhibit infection-decreasing properties.

In the present context the term infection-decreasing effect relates to a treating or preventive effect by the enamel matrix, enamel matrix derivatives and/or enamel matrix proteins on an infection in a tissue of an individual when the tissue or the individual is treated with the enamel matrix, enamel matrix derivatives and/or enamel matrix proteins.

The term infection relates to the invasion and multiplication of microorganisms in body tissues or accumulation on the tissues, which may be clinically inapparent or result in local cellular injury due to competitive metabolism, enzymes, toxins, intracellular replication or antigen-antibody response.

In accordance with the present invention, the infection to be prevented and/or treated may be caused by a microorganism. The microorganisms of interest according to the present invention include bacteria, viruses, yeast, molds, protozoa and rickettsiae.

In the present context the term "anti-bacterial effect" means that the growth of bacteria is suppressed or the bacteria are destroyed. The term is not limited to certain bacteria but encompasses in general any bacteria. However, the invention is focused on i) pathogenic bacteria which cause diseases in mammals including humans and/or ii) bacteria which normally are present in a mammal body and which under certain conditions may cause unwanted conditions in the body.

Accordingly, the invention relates to the use of an active enamel substance for the prevention of or treatment of bacterial growth on a body surface such as the skin, a mucosal surface or a nail or a tooth surface.

General and Specific Description of the Bacterial Conditions to be Counteracted

The enamel matrix, enamel matrix derivatives and/or enamel matrix proteins may be used for the treatment of an infection caused by bacteria together with or without the presence of an antimicrobial. Gram negative bacteria to be treated with the active enamel substance could be cocci, such as *Neisseria* (e.g. *N. meningitis, N. gonorrhoeae*), and *Acinetobacter* or rods, such as *Bacteroides* (e.g. *B. fragilis*), *Bordetella* (e.g. *B. pertussis B. parapertussis*), *Brucella* (e.g. *B. melitentis, B. abortus Bang, B. suis*), *Campylobacter* (e.g. *C. jejuni, C. coli, C. fetus*), *Citrobacter, Enterobacter, Escherichia* (e.g. *E. coli*), *Haemophilus* (e.g. *H. influenzae, H. parainfluenzae*), *Klebsiella* (e.g. *K. pneumoniae*), *Legionella* (e.g. *L. pneumophila*), *Pasteurella* (e.g. *P. yersinia, P. multocida*), *Proteus* (e.g. *P. mirabilis, P. vulgaris*), *Pseudomonas* (e.g. *P. aeruginosa, P. pseudomallei, P. mallei*), *Salmonella* (e.g. *S. enteritidis, S. infantitis S. Dublin S. typhi, S. paratyphi, S. schottmülleri, S. choleraesuis, S. typhimurium*, or any of the 2.500 other serotypes), *Serratia* (e.g. *S. marscences, S. liquifaciens*), *Shigella* (e.g. *S. sonnei, S. flexneri, S. dysenteriae, S. boydii*), *Vibrio* (e.g. *V. cholerae, V. el tor*), and *Yersinia* (e.g. *Y. enterocolitica, Y. pseudotuberculosis, Y. pestis*). Gram positive bacteria to be treated with the active enamel substance could be cocci, such as

*Streptococcus* (e.g. *S. pneumoniae, S. viridans, S. faecalis, S. pyogenes*), *Staphylococcus* (e.g. *S. aureus, S. epidermidis, S. saprophyticus, S. albus*), and rods, such as *Actinomyces* (e.g. *A. israelli*), *Bacillus* (e.g. *B. cereus, B. subtilis, B. anthracis*), *Clostridium* (e.g. *C. botulinum, C. tetani, C. perfringens, C. difficile*), *Corynebacterium* (e.g. *C. diphtheriae*), *Listeria*, and *Providencia*. Other bacteria causing infection include *Propionobacterium acne* and *Pityosporon ovale*.

The enamel matrix, enamel matrix derivatives and/or enamel matrix proteins may also be used for the treatment of an infection caused by a spirochete such as, e.g., *Borrelia, Leptospira, Treponema* or *Pseudomonas*.

An antimicrobial to be used in combination with the enamel matrix, enamel matrix derivatives and/or enamel matrix proteins could be an antimicrobial that has an antimicrobial action through inhibition of cell wall synthesis, such as β-lactams and vancomycin, preferably penicillins, such as amdinocillin, ampicillin, amoxicillin, azlocillin, bacampicillin, benzathine pinicillin G, carbenicillin, cloxacillin, cyclacillin, dicloxacillin, methicillin, meziocillin, nafcillin, oxacillin, penicillin G, penicillin V, piperacillin, and ticarcillin;

cephalosporins, such as the first generation drugs cefadroxil, cefazolin, cephalexin, cephalothin, cephapirin, and cephradine, the second generation drugs cefaclor, cefamandole, cefonicid, ceforamide, cefoxitin, and cefuroxime, or the third generation cephalosporins cefoperazone, cefotaxime, cefotetan, ceftazidime, ceftizoxime, ceftriaxone, and moxalactam; carbapenems such as imipenem; or monobactams such as aztreonam.

Other antimicrobial drugs with action through inhibition of protein synthesis, such as chloramphenicol; other tetracyclines preferably demeclocycline, doxycycline, methacycline, minocycline, and oxytetracycline; aminoglycosides such as amikacin, gentamicin, kanamycin, neomycin, netilmicin, paromomycin, spectinomycin, streptomycin, and tobramycin; polymyxins such as colistin, colistimathate, and polymyxin B, and erythromycins and lincomycins;

antimicrobials with action through inhibition of nucleic acid synthesis in particular sulfonamides such as sulfacytine, sulfadiazine, sulfisoxazole, sulfamethoxazole, sulfamethizole, and sulfapyridine; trimethoprim, quinolones, novobiocin, pyrimethamine, and rifampin.

In a specific embodiment of the invention, the infection is present in the oral cavity and the infection may be a bacterial condition.

Oral bacteria to be contact inhibited or otherwise combated. Examples (not conditions) include bacteria causing caries, e.g. *Streptococcus mutans, Lactobacillus* spp.

bacteria causing periodontal disease e.g. *Actinobacillus actinomycetemcomitans, Porphyromonas gingivalis, Prevotella intermedia, Peptostreptococcus micros, Campylobacter (Fusobacteria, Staphylococci), B. forsythus* bacteria causing alveolitis etc., e.g. *Staphylococcus, Actinomyces* and *Bacillus* bacteria causing periapical lesions, e.g. Spirochetes and all above

Anti-Inflammatory Effect

The present invention also relates to the uses of enamel matrix, enamel matrix derivatives and/or enamel matrix proteins as therapeutic or prophylactic agents having an anti-inflammatory effect.

Several drugs are employed to suppress the manifestations of inflammation, including the adrenocorticosteroids, the large group comprising the so called non-steroid anti-inflammatory drugs or NSAIDs, and drugs such as immunosuppressive agents.

Adrenocorticosteroids, and especially glucocorticoids, have potent anti-inflammatory effects when used in pharmacological doses. They specifically inhibit the early vascular phase of the inflammatory process by decreasing the vascular permeability and thereby granulocyte migration. Glucocorticoids also interfere with late inflammatory and reparative processes, in that they inhibit the proliferation of mesenchymal cells and the production of extracellular macromolecules, including proteoglycanes and collagen. It has been shown experimentally that glucocorticoids inhibit, for example, macrophage function, production of humoral antibodies, cellular immunity, and possibly the release of lysosomal enzymes.

The severity of tissue damage may depend on the antigen/antibody reaction of the organism as well as the degree of retention of inflammatory products in the affected area. Accumulation of mediators of local inflammation accelerates the process. In most cases the process is slow, with immunoinfiltration of the tissue and formation of granulation tissue which contains inflammatory cells.

In the present context the term "anti-inflammatory effect" denotes a counteracting or suppression of inflammation.

General and Specific Description of the Kind of Inflammatory Conditions to be Treated The inflammatory condition to be treated in accordance with the present invention may of course be any inflammatory condition in/on any part of the body or any inflammatory condition present in soft or hard tissue. In one embodiment of the invention the inflammatory condition is present in the oral cavity. Examples of conditions in the oral cavity are alveolitis, cheilitis, bone necrosis (after trauma), fractures.

In another embodiment of the invention, the inflammatory condition is present in a bone donor site. In a third embodiment of the invention, the inflammatory condition is present in a joint cavity. Examples of such inflammatory conditions are rheumatoid arthritis and related conditions.

Anti-Bacterial Versus Anti-Inflammatory

In contrast to many currently used antibiotic agents, enamel matrix proteins will not compromise wound healing and the rapid wound healing in turn does not leave room for chronic or long lasting inflammation processes to develop. Also, the reorganisation of proper tissues, such as described after application of enamel matrix derivatives onto periodontal defects, is clearly favoured by a rapid wound healing without bacteria or inflammatory reactions.

The application of enamel matrix, enamel matrix derivatives and/or enamel matrix proteins leads to rapid wound healing of surgical incisions, possibly by creating a surface which in contact with bacteria inhibit their growth but a the same time enhances fibroblast migration and collagen synthesis. If the inflammatory stage is shortened, the typical signs such as warmth, redness, oedema and pain are less noticeable.

Enamel Matrix, Enamel Matrix Derivatives and Enamel Matrix Proteins

Enamel matrix is a precursor to enamel and may be obtained from any relevant natural source, i.e. a mammal in which teeth are under development. A suitable source is developing teeth from slaughtered animals such as, e.g., calves, pigs or lambs. Another source is for example fish skin.

Enamel matrix can be prepared from developing teeth as described previously (EP-B-0 337 967 and EP-B-0 263 086). The enamel matrix is scraped off and enamel matrix derivatives are prepared, e.g. by extraction with aqueous solution such as a buffer, a dilute acid or base or a water/solvent mixture, followed by size exclusion, desalting or other purification steps, optionally followed by freeze-drying. Enzymes may be deactivated by treatment with heat or solvents, in which case the derivatives may be stored in liquid form without freeze-drying.

In the present context, enamel matrix derivatives are derivatives of enamel matrix which include one or several of enamel matrix proteins or parts of such proteins, produced naturally by alternate splicing or processing, or by either enzymatic or chemical cleavage of a natural length protein, or by synthesis of polypeptides in vitro or in vivo (recombinant DNA methods or cultivation of diploid cells). Enamel matrix protein derivatives also include enamel matrix related polypeptides or proteins. The polypeptides or proteins may be bound to a suitable biodegradable carrier molecule, such as polyamino acids or polysaccharides, or combinations thereof. Furthermore, the term enamel matrix derivatives also encompasses synthetic analogous substances.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Daltons or more. Small proteins are called peptides or oligopeptides.

Enamel matrix proteins are proteins which normally are present in enamel matrix, i.e. the precursor for enamel (Ten Cate: Oral Histology, 1994; Robinson: Eur. J. Oral Science, January 1998, 106 Suppl. 1:282-91), or proteins which can be obtained by cleavage of such proteins. In general such proteins have a molecular weight below 120,000 daltons and include amelogenins, non-amelogenins, proline-rich non-amelogenins, amelins (ameloblastin, sheathlin) and tuftelins.

Examples of proteins for use according to the invention are amelogenins, proline-rich non-amelogenins, tuftelin, tuft proteins, serum proteins, salivary proteins, amelin, ameloblastin, sheathlin, and derivatives thereof, and mixtures thereof. A preparation containing an active enamel substance for use according to the invention may also contain at least two of the aforementioned proteinaceous substances. A commercial product comprising amelogenins and possibly other enamel matrix proteins is marketed as EMDOGAIN® (Biora AB).

In general, the major proteins of an enamel matrix are known as amelogenins. They constitute about 90% w/w of the matrix proteins. The remaining 10% w/w includes proline-rich non-amelogenins, tuftelin, tuft proteins, serum proteins and at least one salivary protein; however, other proteins may also be present such as, e.g., amelin (ameloblastin, sheathlin) which have been identified in association with enamel matrix. Furthermore, the various proteins may be synthesized and/or processed in several different sizes (i.e. different molecular weights). Thus, the dominating proteins in enamel matrix, amelogenins, have been found to exist in several different sizes which together form supramolecular aggregates. They are markedly hydrophobic substances which under physiologically conditions form aggregates. They may carry or be carriers for other proteins or peptides.

Other protein substances are also contemplated to be suitable for use according to the present invention. Examples include proteins such as proline-rich proteins and polyproline. Other examples of substances which are contemplated to be suitable for use according to the present invention are aggregates of such proteins, of enamel matrix derivatives and/or of enamel matrix proteins as well as metabolites of enamel matrix, enamel matrix derivatives and enamel matrix proteins. The metabolites may be of any size ranging from the size of proteins to that of short peptides.

As mentioned above, the proteins, polypeptides or peptides for use according to the invention typically have a molecular weight of at the most about 120 kDa such as, e.g., at the most 100 kDa, 90 kDa, 80 kDa, 70 kDa or 60 kDa as determined by SDS Page electrophoresis.

The proteins for use according to the invention are normally presented in the form of a preparation, wherein the protein content of the active enamel substance in the preparation is in a range of from about 0.05% w/w to 100% w/w such as, e.g., about 5-99% w/w, about 10-95% w/w, about 15-90% w/w, about 20-90% w/w, about 30-90% w/w, about 40-85% w/w, about 50-80% w/w, about 60-70% w/w, about 70-90% w/w, or about 80-90% w/w.

A preparation of an active enamel substance for use according to the invention may also contain a mixture of active enamel substances with different molecular weights.

The proteins of an enamel matrix can be divided into a high molecular weight part and a low molecular weight part, and it has been found that a well-defined fraction of enamel matrix proteins possesses valuable properties with respect to treatment of periodontal defects (i.e. periodontal wounds). This fraction contains acetic acid extractable proteins generally referred to as amelogenins and constitutes the low molecular weight part of an enamel matrix (cf. EP-B-0 337 967 and EP-B-0 263 086).

As discussed above the low molecular weight part of an enamel matrix has a suitable activity for inducing binding between hard tissues in periodontal defects. In the present context, however, the active proteins are not restricted to the low molecular weight part of an enamel matrix. At present, preferred proteins include enamel matrix proteins such as amelogenin, amelin, tuftelin, etc. with molecular weights (as measured in vitro with SDS-PAGE) below about 60,000 daltons but proteins having a molecular weight above 60,000 daltons have also promising properties as candidates for wound healing, anti-bacterial and/or anti-inflammatory agents.

Accordingly, it is contemplated that the active enamel substance for use according to the invention has a molecular weight of up to about 40,000 such as, e.g. a molecular weight of between about 5,000 and about 25,000.

Within the scope of the present invention are also peptides as described in WO 97/02730, i.e. peptides which comprise at least one sequence element selected from the group consisting of the tetrapeptides DGEA (Asp-Gly-Glu-Ala) (residues 370-373 of SEQ ID NO.: 1), VTKG (Val-Thr-Lys-Gly) (residues 277-280 of SEQ ID NO.: 1), EKGE (Glu-Lys-Gly-Glu) (residues 282-285 of SEQ ID NO.: 1), and DKGE (Asp-Lys-Gly-Glu) (residues 298-301 of SEQ ID NO.: 1) and which further comprise an amino acid sequence from which a consecutive string of 20 amino acids is identical to a degree of at least 80% with a string of amino acids having the same length selected from the group consisting of the amino acid sequence shown in SEQ ID NO:

1 and a sequence consisting of amino acids 1 to 103 of SEQ ID NO: 1 and amino acids 6 to 324 of SEQ ID NO:2.

By the term "sequence identity" is meant the identity in sequence of amino acids in the match with respect to identity and position of the amino acids of the peptides. A gap is counted as non-identity for one or more amino acids as appropriate.

Such peptides may comprise from 6 to 300 amino acids, e.g. at least 20 amino acids, at least 30 amino acids, such as at least 60 amino acids, at least 90 amino acids, at least 120 amino acids, at least 150 amino acids or at least 200 amino acids.

A method for the isolation of enamel matrix proteins involves extraction of the proteins and removal of calcium and phosphate ions from solubilized hydroxyapatite by a suitable method, e.g. gel filtration, dialysis or ultrafiltration (see e.g. Janson, J-C & Rydén, L. (Eds.), Protein purification, VCH Publishers 1989 and Harris, ELV & Angal, S., Protein purification methods—A practical approach, IRL Press, Oxford 1990).

A typical lyophilized protein preparation may mainly or exclusively up to 70-90% contain amelogenins with a molecular weight (MW) between 40,000 and 5,000 daltons, the 10-30% being made up of smaller peptides, salts and residual water. The main protein bands are at 20 kDa, 12-14 kDa and around 5 kDa.

By separating the proteins, e.g. by precipitation, ion-exchange chromatography, preparative electrophoresis, gel permeation chromatography, reversed phase chromatography or affinity chromatography, the different molecular weight amelogenins can be purified.

The combination of molecular weight amelogenins may be varied, from a dominating 20 kDa compound to an aggregate of amelogenins with many different molecular weights between 40 and 5 kDa, and to a dominating 5 kDa compound. Other enamel matrix proteins such as amelin, tuftelin or proteolytic enzymes normally found in enamel matrix, can be added and carried by the amelogenin aggregate.

As an alternative source of the enamel matrix derivatives or proteins one may also use generally applicable synthetic routes well-known for a person skilled in the art or use cultivated cells or bacteria modified by recombinant DNA-techniques (see, e.g., Sambrook, J. et al.: Molecular Cloning, Cold Spring Harbor Laboratory Press, 1989).

Physico-Chemical Properties of Enamel Matrix, Enamel Matrix Derivatives and Enamel Matrix Proteins In general the enamel matrix, enamel matrix derivatives and enamel matrix proteins are hydrophobic substances, i.e. less soluble in water especially at increased temperatures. In general, these proteins are soluble at non-physiological pH values and at a low temperature such as about 4-20° C., while they will aggregate and precipitate at body temperature (35-37° C.) and neutral pH.

The enamel matrix, enamel matrix derivatives and/or enamel matrix proteins for use according to the invention also include an active enamel substance, wherein at least a part of the active enamel substance is in the form of aggregates or after application in vivo is capable of forming aggregates. The particle size of the aggregates is in a range of from about 20 nm to about 1 µm.

It is contemplated that the solubility properties of enamel matrix, enamel matrix derivatives and/or enamel matrix proteins are of importance in connection with the prophylactic and therapeutic activity of the substances. When a composition containing the enamel matrix, enamel matrix derivatives and/or enamel matrix proteins (in the following also denoted "active enamel substance" as a common term) is administered to e.g. a human, the proteinaceous substances will precipitate due to the pH normally prevailing under physiological conditions. Thus, a layer of enamel matrix, enamel matrix derivatives and/or enamel matrix proteins is formed at the application site and this layer (which also may be a molecular layer in those cases where aggregates have been formed) is difficult to rinse off under physiological conditions. Furthermore, due to the substances bioadhesive properties (see below) the precipitated layer is firmly bound to the tissue also at the margin between the precipitated layer and the tissue. The proteinaceous layer thus covers the tissue onto which the enamel matrix, enamel matrix derivatives and/or enamel matrix proteins or compositions thereof have been applied and the active enamel substances are maintained in situ for a prolonged period of time, i.e. it is not necessary to administer the active enamel substance(s) with short intervals. Furthermore, the layer formed in situ can almost be compared to an occlusive dressing, i.e. the layer formed protects the tissue onto which the layer is formed from the surroundings. In the case of a wound tissue, an infected tissue or an inflamed tissue such a layer protects the tissue from further contamination from microorganisms present in the surroundings. Furthermore, the proteinaceous layer may exert its effect by direct contact with the tissue or with microorganisms present in/on/at the tissue.

In order to enable a proteinaceous layer to be formed in situ after application it may be advantageous to incorporate a suitable buffer substance in a pharmaceutical or cosmetic composition of the enamel matrix, enamel matrix derivatives and/or enamel matrix proteins; the purpose of such a buffer substance could be to avoid the dissolution of the active enamel substance at the application site.

The enamel matrix, enamel matrix derivatives and enamel matrix proteins have also been observed (by the present inventors) to posses bioadhesive properties, i.e. they have an ability to adhere to skin or mucosal surfaces. These properties are most valuable in connection with a therapeutic and/or prophylactic treatment at least for the following reasons:

the prophylactically and/or therapeutically active substance(s) can be maintained at the application site for a prolonged period of time (i.e. i) the administration frequency can be reduced, ii) a controlled release effect of the active substance is obtainable and/or iii) a local treatment at the application site is improved)

the substances may in themselves be suitable as vehicles for other prophylactically or therapeutically active substances because a vehicle containing enamel matrix, enamel matrix derivatives and/or enamel matrix proteins can be formulated as a bioadhesive vehicle (i.e. a novel bioadhesive drug delivery system based on the bioadhesive properties of enamel matrix, enamel matrix derivatives and/or enamel matrix proteins).

Theories with Respect to Mechanism of Action

Enamel matrix is an example of an extracellular protein matrix which adheres to mineral surfaces as well as to proteinaceous surfaces. At physiological pH and temperature the proteins form an insoluble supra-molecular aggregate (Fincham et al. in J. Struct. Biol. 1994 March-April; 112 (2):103-9 and in J. Struct. Biol. 1995 July-August; 115 (1):50-9), which is gradually degraded by proteolytic enzymes (occurs both in vivo and in vitro provided that the proteases have not been subjected to inactivation).

The recent observation that enamel matrix is formed and temporarily present during root and root cementum formation can explain how application of enamel matrix, enamel matrix derivatives and/or enamel matrix proteins promotes the regeneration of periodontal tissue. However, the observation underlying the present invention that enamel matrix, enamel matrix derivatives and/or enamel matrix proteins also have a positive effect on healing of soft tissue defects like wound healing is very surprising. The same applies to the observations with respect to anti-infectious and anti-inflammatory effect.

In many species, remnants of enamel matrix are found in the newly mineralized crown when a tooth is erupting into the oral cavity. It might be argued that a new tooth would be very vulnerable to bacterial attack from common oral bacteria unless it had a natural protection during this initial phase.

Application of insolubilising enamel matrix, enamel matrix derivatives and/or enamel matrix proteins with suitable anti-bacterial and/or anti-inflammatory properties onto a wounded surface will enhance and improve healing.

As demonstrated in the experimental section herein the enamel matrix, enamel matrix derivatives and/or enamel matrix proteins or protein aggregates hinder bacterial growth by contact inhibition, while exposed cells apparently react upon the enamel matrix as a normal environment which suppresses inflammatory responses.

In accordance with the present invention, an enamel matrix, enamel matrix derivative and/or enamel matrix protein may be used for curative purposes as well as for preventive purposes. Furthermore, an enamel matrix, enamel matrix derivative and/or enamel matrix protein may be used together with other active drug substances such as, e.g. anti-bacterial, anti-inflammatory, antiviral, antifungal substances or in combination with growth factors such as, e.g., TGF$\beta$, PDGF, IGF, FGF, keratinocyte growth factor or peptide analogues thereof (it is believed that EGF promotes healing by enhancing migration and cell division of epithelial cells; furthermore, EGF increases fibroblast numbers in wounds resulting in a greater collagen production). Enzymes—either inherently present in the enamel matrix or preparation thereof or added—may also be used in combination with an enamel matrix, enamel matrix derivative and/or enamel matrix protein, especially proteases.

A preparation of the active enamel substance is normally formulated as a pharmaceutical or cosmetic composition. Such a composition may of course consist of the proteinaceous preparation or it may further comprise a pharmaceutically or cosmetically acceptable excipient. Especially suitable excipients for use in pharmaceutic or cosmetic compositions are propylene glycol alginate, or hyaluronic acid or salts or derivatives thereof.

Pharmaceutical and/or Cosmetic Compositions

In the following examples of suitable compositions containing the active enamel substance(s) are given. Depending on the use of the active enamel substance(s), a composition may be a pharmaceutical or a cosmetic composition. In the following the term "pharmaceutical composition" is also intended to embrace cosmetic compositions as well as compositions belonging to the so-called grey area between pharmaceuticals and cosmetics, namely cosmeceuticals.

For the administration to an individual (an animal or a human) the enamel matrix, enamel matrix derivatives and/or enamel matrix proteins (in the following also denoted "active enamel substance") and/or a preparation thereof are preferably formulated into a pharmaceutical composition containing the active enamel substance and, optionally, one or more pharmaceutically acceptable excipients.

The compositions may be in form of, e.g., solid, semi-solid or fluid compositions such as, e.g., bioabsorbable patches, drenches, dressings, hydrogel dressings, hydrocolloid dressings, films, foams, sheets, bandages, plasters, delivery devices, implants, powders, granules, granulates, capsules, agarose or chitosan beads, tablets, pills, pellets, microcapsules, microspheres, nanoparticles, sprays, aerosols, inhalation devices, gels, hydrogels, pastes, ointments, creams, soaps, suppositories, vagitories, tooth paste, solutions, dispersions, suspensions, emulsions, mixtures, lotions, mouthwash, shampoos, enemas, kits containing e.g. two separate containers, wherein the first one of the containers contains the active enamel substance optionally admixed with other active drug substance(s) and/or pharmaceutically acceptable excipients and the second container containing a suitable medium intended to be added to the first container before use in order to obtain a ready-to-use composition;

and in other suitable forms such as, e.g., implants or coating of implants or in a form suitable for use in connection with implantation or transplantation.

Compositions for application to the skin or to the mucosa are considered most important in connection with the present invention. Thus, a composition comprising the active enamel substance to be administered may be adapted for administration by any suitable route, for example by topical (dermal), oral, buccal, nasal, aural, rectal or vaginal administration, or by administration to a body cavity such as, e.g., a tooth root or a tooth root canal. Furthermore, a composition may be adapted to administration in connection with surgery, e.g. in connection with incision within the body in order to promote healing of internal wounds and soft tissue damages.

As mentioned above, a composition of the active enamel substance(s) may be suitable for use during surgery, e.g. for local application (e.g. in the oral cavity) in the form of a gel, film or dry pellet, or as a rinsing solution or treatment with a paste or cream on tissue or surfaces to prevent bacterial attack. In connection with surgery or implantation in the area of the tooth root canal, a paste for cavity sealing can be employed.

The compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

As mentioned above, the application of a composition comprising an active enamel substance is intended for skin or mucosa. Other applications may of course also be relevant such as, e.g., application on dentures, prostheses, implants, and application to body cavities such as the oral, nasal and vaginal cavity. The mucosa is preferably selected from oral, buccal, nasal, aural, rectal and vaginal mucosa. Furthermore, the application may be directly on or onto a wound or other soft tissue injuries.

Furthermore, application within the dental/odontologic area is also of great importance. Relevant examples are application to periodontal (dental) pockets, to gingiva or to gingival wounds or other wounds located in the oral cavity, or in connection with oral surgery.

It is further anticipated that, due to the antibacterial properties of the active enamel substance described herein, it may advantageously be applied to teeth or tooth roots for the prevention of caries and/or plaque. To support this use, it has been shown (Weinmann, J. P. et al: Hereditary disturbances of enamel formation and calcification, J. Amer. Dent. Ass. 32: 397-418, 1945; Sundell S, Hereditary amelogenesis imperfecta. An epidemiological, genetic and clinical study in a Swedish child population, Swed Dent J Suppl 1986; 31: 1-38) that teeth which are imperfectly developed (amelogenesis imperfecta) and consequently contain large amounts of amelogenins are remarkably caries resistant.

A pharmaceutical composition comprising an active enamel substance serves as a drug delivery system. In the present context the term "drug delivery system" denotes a pharmaceutical composition (a pharmaceutical formulation or a dosage form) which upon administration presents the active substance to the body of a human or an animal. Thus, the term "drug delivery system" embraces plain pharmaceutical compositions such as, e.g., creams, ointments, liquids, powders, tablets, etc. as well as more sophisticated formulations such as sprays, plasters, bandages, dressings, devices, etc.

Apart from the active enamel substance, a pharmaceutical composition for use according to the invention may comprise pharmaceutically or cosmetically acceptable excipients.

A pharmaceutically or cosmetically acceptable excipient is a substance which is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

Whether a pharmaceutically acceptable excipient is suitable for use in a pharmaceutical composition is generally dependent on which kind of dosage form is chosen for use for a particular kind of wound. In the following are given examples of suitable pharmaceutically acceptable excipients for use in different kinds of compositions for use according to the invention.

In the following is given a review on relevant pharmaceutical compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

The choice of pharmaceutically acceptable excipient(s) in a composition for use according to the invention and the optimum concentration thereof cannot generally be predicted and must be determined on the basis of an experimental evaluation of the final composition. However, a person skilled in the art of pharmaceutical formulation can find guidance in e.g., "Remington's Pharmaceutical Sciences", 18th Edition, Mack Publishing Company, Easton, 1990.

Topical Compositions

For application to the mucosa or the skin, the compositions for use according to the invention may contain conventionally non-toxic pharmaceutically acceptable carriers and excipients including microspheres and liposomes.

The compositions for use according to the invention include all kinds of solid, semi-solid and fluid compositions. Compositions of particular relevance are e.g. pastes, ointments, hydrophilic ointments, creams, gels, hydrogels, solutions, emulsions, suspensions, lotions, liniments, shampoos, jellies, soaps, sticks, sprays, powders, films, foams, pads, sponges (e.g. collagen sponges), pads, dressings (such as, e.g., absorbent wound dressings), drenches, bandages, plasters and transdermal delivery systems.

The pharmaceutically acceptable excipients may include solvents, buffering agents, preservatives, humectants, chelating agents, antioxidants, stabilizers, emulsifying agents, suspending agents, gel-forming agents, ointment bases, penetration enhancers, perfumes, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethylamine etc.

Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of chelating agents are sodium EDTA and citric acid.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol aginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes.

Examples of hydrophilic ointment bases are solid macrogols (polyethylene glycols).

Other examples of ointment bases are triethanolamine soaps, sulphated fatty alcohol and polysorbates.

Examples of powder components are: alginate, collagen, lactose, powder which is able to form a gel when applied to a wound (absorbs liquid/wound exudate). Normally, powders intended for application on large open wounds must be sterile and the particles present must be micronized.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and kitosans.

Dressings and/or bandages are also important delivery systems for an active enamel substance. When dressings are used as dosage form, the active enamel substance may be admixed with the other material/ingredients before or during the manufacture of the dressing or, the active enamel substance may in some way be coated onto the dressing e.g. by dipping the dressing in a solution or dispersion of the active enamel substance or by spraying a solution or dispersion of the active enamel substance onto the dressing. Alternatively, the active enamel substance may be applied in the form of a powder to the dressing. Dressings may be in the form of absorbent wound dressings for application to exuding wounds. Dressings may also be in the form of hydrogel dressings (e.g. cross-linked polymers such as, e.g. Intrasite® which contains carboxymethylcellulose, propylene glycol or polysaccharide, disaccharide and proteins) or in the form of occlusive dressings such as, e.g., alginates, chitosan, hydrophilic polyurethane film, collagen sheets, plates, powders, foams, or sponges, foams (e.g. polyurethane or silicone), hydrocolloids (e.g. carboxymethylcellulose, CMC), collagen and hyaluronic acid-based dressings including combinations thereof.

Alginate, chitosan and hydrocolloid dressings take up wound exudate when placed on a wound. When doing so they produce an aqueous gel on the surface of the wound and this gel is believed to be beneficial for the healing of the wound due to the retaining of moisture in the wound.

It is also envisaged that the active enamel substance may be incorporated in a tissue adhesive also comprising, e.g. fibrinogen and thrombin and optionally Factor XIII or another plasma coagulation factor to provide hemostasis. The tissue adhesive may either be prepared as a premix of the active enamel substance, fibrinogen and optionally Factor XIII, thrombin being added to the premix immediately before the tissue adhesive is applied on the wound. Alternatively, the premix of fibrinogen and active enamel substance and optionally Factor XIII may be applied on the wound before application of thrombin. In situ, the thrombin converts fibrinogen to fibrin thereby reproducing the coagulation process occurring naturally in wound healing. The presence of the active enamel substance in the tissue adhesive may serve to accelerate the wound healing process as discussed above. A commercial product suitable for inclusion of the active enamel substance is Tisseel®, a two-component fibrin sealant produced by Immuno, AG, Vienna, Austria.

In a toothpaste or mouthwash formulation or other formulation for application to teeth or tooth roots, the active enamel substance may either be present in a dissolved state in a vehicle of slightly acid pH or as a dispersion in a vehicle of neutral pH. It is anticipated that in use the active enamel substance may form a protective layer on the surface of the teeth, thereby preventing the attachment of caries producing bacteria (cf. Example 4 below). In such dental care preparations, the active enamel substance may be formulated together with one or more other compounds which have a caries preventive effect, notably fluorine or another trace element such as vanadium or molybdenum. At neutral pH, the trace element is believed to be bound to (e.g. by ion bonds) or embedded in the active enamel substance from which it is released to exert its caries preventive effect when the active enamel substance is dissolved at a pH of about 5.5 or less, e.g. due to acid production by caries producing bacteria.

The compositions mentioned above for topical administration are most suitably for application directly to wounds or they may be suitable for application to or for introduction into relevant orifice(s) of the body, e.g. the rectal, urethral, vaginal, aural, nasal or oral orifices. The composition may simply be applied directly on the part to be treated such as, e.g., on the mucosa, or by any convenient route of administration.

Compositions which have proved to be of importance in connection with topical application are those which have thixotropic properties, i.e. the viscosity of the composition is affected e.g. by shaking or stirring so that the viscosity of the composition at the time of administration can be reduced and when the composition has been applied, the viscosity increases so that the composition remains at the application site.

Compositions for Oral Use or for Application to Mucosa or Skin

Suitable compositions for use according to the invention may also be presented in the form of suspensions, emulsions or dispersions. Such compositions contains the active enamel substance in admixture with a dispersing or wetting agent, suspending agent, and/or one or more preservatives and other pharmaceutically acceptable excipients. Such compositions may also be suitable for use in the delivery of the active enamel substance to e.g. an intact or damaged mucosa such as the oral, buccal, nasal, rectal, or vaginal mucosa, or for administration to intact or damaged skin, or wounds.

Suitable dispersing or wetting agents are, for example, naturally occurring phosphatides, e.g., lecithin, or soybean lecithin; condensation products of ethylene oxide with e.g. a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate, etc.

Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g. Avicel® RC 591, methylcellulose); alginates and chitosans such as, e.g., sodium alginate, etc.

Suitable examples of preservatives for use in compositions according to the invention are the same as those mentioned above.

Compositions for use according to the invention may also be administered by the oral route. Suitable oral compositions may be in the form of a particulate formulation or in the form of a solid, semi-solid or fluid dosage form.

Compositions for oral use include solid dosage forms such as, e.g., powders, granules, granulates, sachets, tablets, capsules, effervescent tablets, chewable tablets, lozenges, immediate release tablets, and modified release tablets as well as fluid or liquid formulations such as, e.g. solutions, suspensions, emulsions, dispersions, and mixtures. Furthermore, composition may be in the form of powders, dispersible powders, or granules suitable for preparation of an aqueous suspension by addition of a liquid medium such as, e.g. an aqueous medium, With respect to solid dosage forms for oral (or topical use) a composition for use according to the invention normally contains the active enamel substance and any further active substance optionally in admixture with one or more pharmaceutically acceptable excipients. These excipients may be, for example, inert diluents or fillers, such as sucrose, sorbitol, sugar, mannitol, microcrystalline cellulose, starches including potato starch, calcium carbonate, sodium chloride, lactose, calcium phosphate, calcium sulfate, or sodium phosphate;

granulating and disintegrating agents, for example, cellulose derivatives including microcrystalline cellulose, starches including potato starch, croscarmellose sodium, alginates, or alginic acid and chitosans;

binding agents, for example, sucrose, glucose, sorbitol, acacia, alginic acid, sodium alginate, gelatin, starch, pregelatinized starch, microcrystalline cellulose, magnesium aluminum silicate, sodium carboxymethylcellulose, methylcellulose, hydroxypropyl methylcellulose, ethylcellulose, polyvinylpyrrolidone, polyvinylacetate, or polyethylene glycol; and chitosans;

lubricating agents including glidants and antiadhesives, for example, magnesium stearate, zinc stearate, stearic acid, silicas, hydrogenated vegetable oils, or talc.

Other pharmaceutically acceptable excipients can be colorants, flavouring agents, plasticizers, humectants, buffering agents, etc.

In those cases where the pharmaceutical composition is in the form of a solid dosage form in unit dosage form (e.g. a tablet or a capsule), the unit dosage form may be provided with a coating like one or more of the coatings mentioned below.

In those cases where the composition is in the form of a tablet, capsule or a multiple unit composition, the composition or the individual units or a tablet or a capsule containing the individual units may be coated e.g. with a sugar coating, a film coating (e.g. based on hydroxypropyl methylcellulose, methylcellulose, methyl hydroxyethylcellulose, hydroxypropylcellulose, carboxymethylcellulose, acrylate copolymers (Eudragit), polyethylene glycols and/or polyvinylpyrrolidone) or an enteric coating (e.g. based on methacrylic acid copolymer (Eudragit), cellulose acetate phthalate, hydroxypropyl methylcellulose phthalate, hydroxypropyl methylcellulose acetate succinate, polyvinyl acetate phthalate, shellac and/or ethylcellulose). Furthermore, a time delay material such as, e.g., glyceryl monostearate or glyceryl distearate may be employed.

Rectal and/or Vaginal Compositions

For application to the rectal or vaginal mucosa, suitable compositions according to the invention include suppositories (emulsion or suspension type), enemas, and rectal gelatin capsules (solutions or suspensions). Appropriate pharmaceutically acceptable suppository bases include cocoa butter, esterified fatty acids, glycerinated gelatin, and various water-soluble or dispersible bases like polyethylene glycols and polyoxyethylene sorbitan fatty acid esters. Various additives like, e.g., enhancers or surfactants may be incorporated.

Nasal Compositions

For application to the nasal mucosa (as well as to the oral mucosa), sprays and aerosols for inhalation are suitable compositions according to the invention. In a typical nasal composition, the active enamel substance is present in the form of a particulate formulation optionally dispersed in a suitable vehicle. The pharmaceutically acceptable vehicles and excipients and optionally other pharmaceutically acceptable materials present in the composition such as diluents, enhancers, flavouring agents, preservatives, etc. are all selected in accordance with conventional pharmaceutical practice in a manner understood by the persons skilled in the art of formulating pharmaceuticals.

Dosages of Enamel Matrix, Enamel Matrix Derivatives and Enamel Matrix Proteins

In a pharmaceutical composition for use according to the invention on skin or mucosa, an active enamel substance is generally present in a concentration ranging from about 0.01% to about 99.9% w/w. The amount of composition applied will normally result in an amount of total protein per $cm^2$ wound/skin/tissue area corresponding to from about 0.01 $mg/cm^2$ to about 20 $mg/cm^2$ such as from about 0.1 $mg/cm^2$ to about 15 $mg/cm^2$.

The amount applied of the composition depends on the concentration of the active enamel substance in the composition and of the release rate of the active enamel substance from the composition, but is generally in a range corresponding to at the most about 15-20 $mg/cm^2$.

In those cases where the active enamel substance is administered in the form of a fluid composition, the concentration of the active enamel substance in the composition is in a range corresponding to from about 0.1 to about 50 mg/ml.

Higher concentrations are in some cases desirable and can also be obtained such as a concentration of at least about 100 mg/ml.

When the composition is applied to the oral cavity, the following doses are relevant:

Experimental defect areas (in monkeys) in the oral cavity typically have a size of about 4×2×5-6 mm corresponding to 50 μl or from about 0.025 to about 0.15 mg total protein/$mm^2$ or about 2.5-15 $mg/cm^2$. Usually up to 0,5 such as, e.g., 0.4, 0.3, 0.2 or 0.1 ml of a composition having a concentration of about 1-40 mg/ml such as, e.g., 5-30 mg/ml is applied.

Defect areas in humans in the oral cavity and due to periodontal diseases typically have a size of about 5-10×2-4×5-10 mm corresponding to about 200 μl and normally at the most about 0.5-1 ml such as about 0.2-0.3 ml per tooth is applied of a composition having a concentration of about 1-40 mg total protein/ml such as, e.g., 5-30 mg/ml is applied. 0.2-0.3 mg/ml corresponds to about 6 mg protein per 25-100 mm or about 0.1 $mg/mm^2$ if calculated only on root surface. Normally an excessive volume is applied to allow coverage of all surfaces. Even a multilayer would only require a small fraction of the above-mentioned amounts.

Generally, about 0.1-0.5 ml such as, e.g., about 0.15-0.3 ml or about 0.25-0.35 ml of a composition comprising the active enamel substance is applied in defect volumes in extraction alveoli (holes after extraction of teeth). The concentration of the active enamel substance in the composition is normally about 1-40 mg total protein/ml such as, e.g., 5-30 mg/ml. When 0.3-0.4 ml is applied of such a composition for wisdom teeth, this volume corresponds to about 0.1 mg/cm$^2$ (alveolus calculated as cylinder with radius 5 mm and height 20 mm).

The concentration of the active enamel substance in a pharmaceutical composition depends on the specific enamel substance, its potency, the severity of the disease to be prevented or treated, and the age and condition of the patient. Methods applicable to selecting relevant concentrations of the active enamel substance in the pharmaceutical composition are well known to a person skilled in the art and may be performed according to established guidelines for good clinical practice (GCP) or Investigational New Drug Exemption ("IND") regulations as described in e.g. International Standard ISO/DIS 14155 Clinical investigation of medical devices, 1994 and ICH (international Committee for Harmonisation): Harmonised tripartite guideline for good clinical practice, Brookwood Medical Publications, Ltd, Surrey, UK, 1996. A person skilled in the art would, by use of the methods described in standard textbooks, guidelines and regulations as described above as well as common general knowledge within the field, be able to select the exact dosage regimen to be implemented for any active enamel substance and/or selected other active substances and dosage form using merely routine experimentation procedures.

In other aspects the invention relates to methods for i) preventing and/or treating wounds, ii) decreasing infection and iii) preventing and/or treating inflammation, the methods comprising administration to a mammal in need of such a treatment an effective amount of an active enamel substance.

As will be understood, details and particulars concerning the use of an active enamel substance for the prevention and/or treatment of wound will be the same as or analogous to the details and particulars concerning the other use aspects (anti-bacterial and anti-inflammatory aspects) and the method aspects discussed above, and this means that wherever appropriate, the statements above concerning an active enamel substance, a preparation containing an active enamel substance, a pharmaceutical composition containing an active enamel substance, preparation of i) an active enamel substance, ii) a preparation containing an active enamel substance, iii) a pharmaceutical composition containing an active enamel substance, as well as improved properties and uses apply mutatis mutandis to all aspects of the invention.

BRIEF DESCRIPTION OF THE DRAWINGS

The invention is further disclosed with reference to the appended drawings wherein.

EXPERIMENTAL SECTION

Materials and Methods

Figure 1:
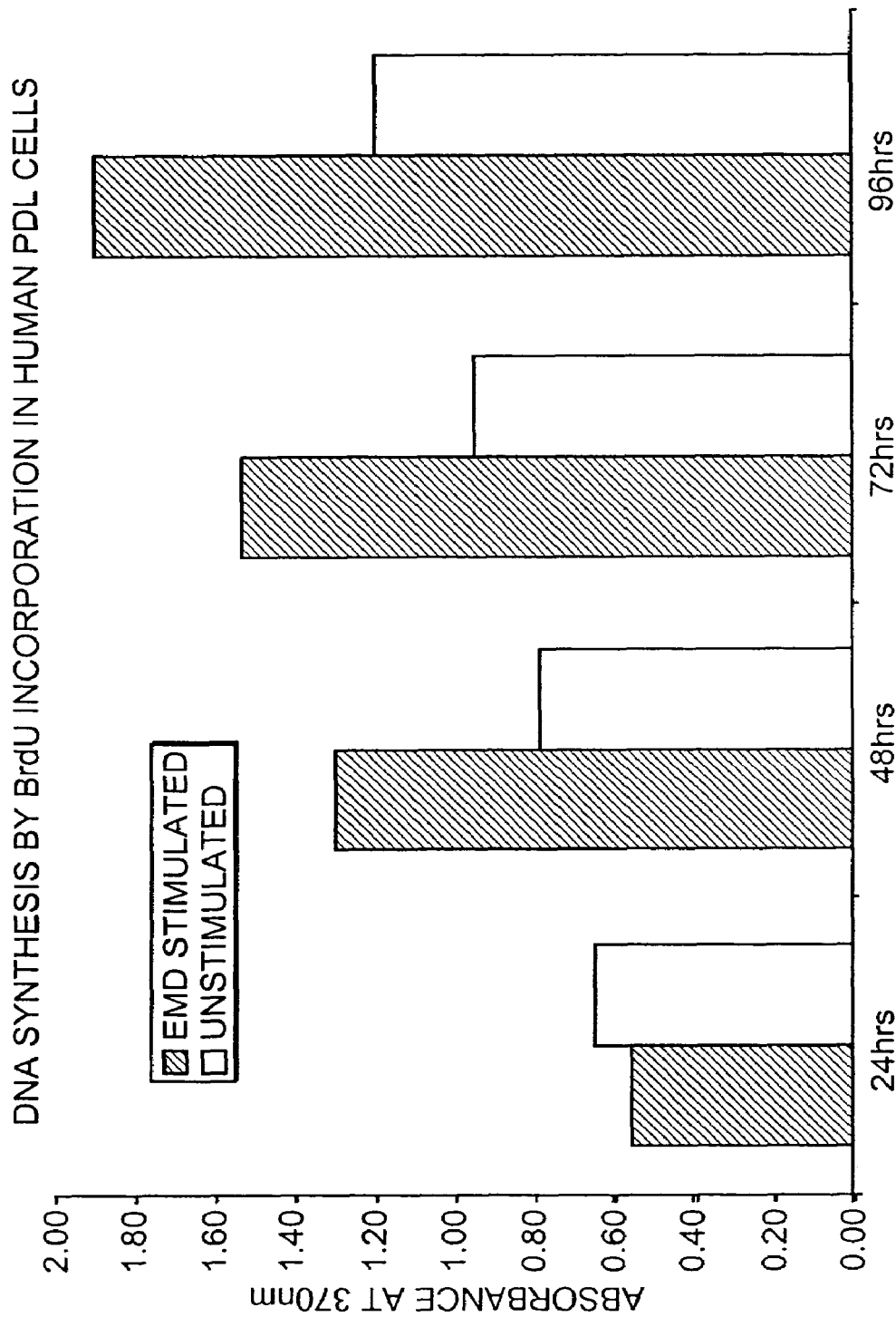
FIG. 1 is a graph showing DNA synthesis in human PDL cells stimulated with EMD or unstimulated cells.

Enamel Matrix Derivative, EMDOGAIN®, from BIORA AB, S-205 12 Malmö, Sweden containing 30 mg freeze-dried Enamel Matrix protein (in the following abbreviated to EMD) and 1 ml Vehicle Solution (Propylene Glycol Alginate), which are mixed prior to application, unless the protein and the Vehicle are tested separately. The weight ratio is about 85/5/10 between the main protein peaks at 20, 14 and 5 kDa, respectively.

Heat-treated EMD is EMD which has been heated for 3 hours at about 80° C. in order to inactivate residual proteases.

Amelogenin 20 kDa protein and Tyrosine Rich Amelogenin Peptide (TRAP) 5 kDa were isolated from EMD using HPLC gel permeation chromatography (TSK G-2000 SW equilibrated with 30% acetonitril in 0.9% NaCl) and purified by reversed phase chromatography (Pro-RPC, HR 5/10, Pharmacia-Upjohn, Sweden) using a gradient of acetonitrile. The separated protein/polypeptides were then added in various amounts to the Vehicle Solution of EMDOGAIN®, unless tested separately.

Hyaluronic acid was HMT-0028 (MW 990,000) from Seikagaku Corporation, Tokyo, Japan Bacteria and yeast were all primarily isolated from patients, classified by metabolic and antigenic properties according to standard procedures. The species of the bacteria and the yeast used are listed in the table below.

Serum Albumin (bovine) and Collagen Type 1 (bovine) were both obtained from Sigma, St. Louis, U.S.A.

The agar plates were all "Brain Hart Infusion agar" from Difco supplemented with human red blood cells (100 ml per litre of agar).

EXAMPLES

Example 1

Cell Proliferation and TGF-β1 Production in PDL Cells Treated with EMDOGAIN®

A stock solution of EMD was prepared by dissolving a vial (containing 30 mg EMD) in 3 ml sterile filtered 0.1% HAc. 60 μl of the EMD stock solution was added to 6000 μl of Dulbecco's Modified Eagle's Medium containing 10% fetal calf serum and 1% of a penicillin-streptomycin solution. 300 μl of the mixture was added to each well of 96-well microtiter plates (NUNC A/S, Denmark, Cat. # 167008). 1000 human periodontal ligament (PDL) cells (obtained from healthy human periodontal tissues of individuals undergoing extractions of premolars for orthodontic reasons, and cultured substantially as described in Somerman et al., J. Dental Res. 67, 1988, pp. 66-70) were added to each well and incubated at 37° C., 5% $CO_2$ for 5 days.

PDL cells used as controls were cultured in Dulbecco's Modified Eagle's Medium substantially as described above, but in the absence of EMD.

After incubation, the cells were subjected to a cell proliferation immunoassay measuring incorporation of 5-bromo-2'-deoxyuridine (BrdU) in accordance with the manufacturer's instructions (Boehringer Mannheim, Cat. # 1647 229). In this procedure, BrdU is incorporated instead of thymidine in the DNA of growing cells. The incorporation of BdrU is detected by ELISA assay, and the amount of BrdU measured in the assay is an indication of the rate of DNA synthesis and consequently rate of cell proliferation of the PDL cells.

The results appear from FIG. 1 showing that PDL cells cultured in the presence of EMD exhibit a significantly higher rate of proliferation than PDL cells cultured in the absence of EMD.

To 100 μl of cell supernatant from the microtiter plate was added 20 μl 1N HCl followed by incubation for 10 minutes at room temperature. The incubation mixture was neutralised with 20 μl 1N NaOH/0.5 M HEPES. 100 μl of this mixture was added to 400 μl of a dilution buffer. 200 μl of the dilution was subjected to ELISA using the Quantikines™ kit (Cat. # DB100) available from R&D Systems, UK, according to the manufacturer's instructions.

Figure 2:
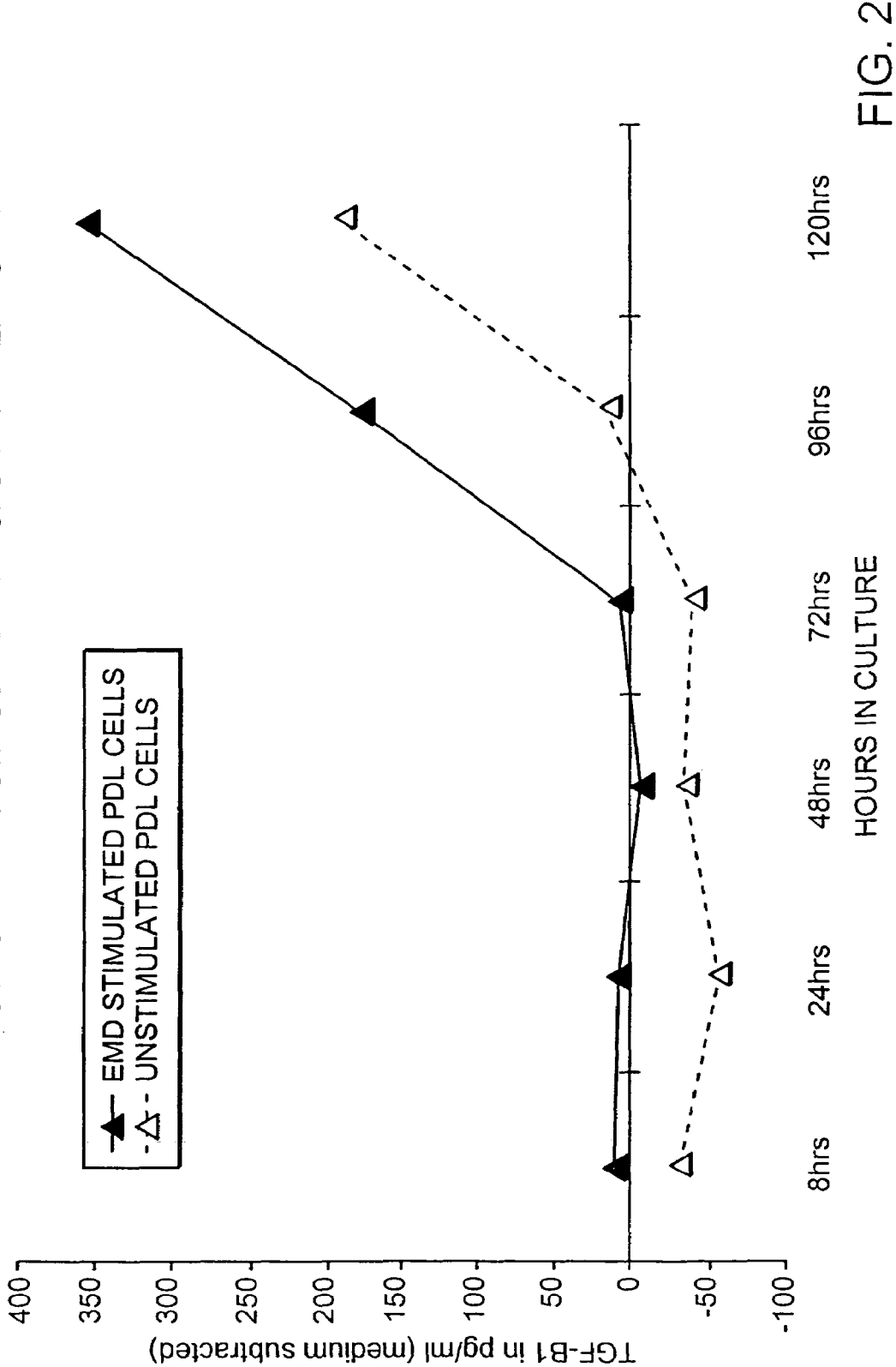
FIG. 2 is a graph showing TGF-β1 production in human PDL cells stimulated with EMD and unstimulated cells.

The results are shown in FIG. 2 showing a pronounced increase in TGF-β1 production in PDL cells incubated with EMD relative to PDL cells not incubated with EMD.

The proteins used in this example were dissolved in phosphate buffered saline (PBS) with pH adjusted to 5.5 with acetic acid. The microbes employed were suspended in PBS pH 6.8 to a final concentration having an $OD_{600}$ of 0.4.

50 microliter of EMDOGAIN® (30 mg of EMD in 1 ml of PGA) and 50 microliter of EMD, heat-treated EMD, EMD fractions A, B, C and H (all 10 mg of protein per ml of PBS buffer) was dripped onto an agar plate and allowed to air dry on top of the plate (9 cm diameter, standard agar for determination of resistance added supplements as required by the individual microbes). A homogenous suspension of microbes (1 ml, $OD_{280}$=0.5) was then added by spreading the suspension on top of the agar plates, and the plates were incubated at 35° C. for 3 days (aerobic cultures) or 14 days (anaerobic cultures) in a $CO_2$ enriched atmosphere or under anaerobic condition according to individual growth requirements. All cultures were inspected daily. Collagen type 1 and Serum albumin (both bovine) were tested under the same conditions as controls. Undiluted propyleneglycolalginate (PGA—EMD vehicle), PBS buffer and hyaluronic acid (HA—alternative EMD vehicle) were also applied as negative controls.

The results are shown in Table 1. Only the enamel matrix derivatives or enamel matrix proteins or derivatives inhibited the growth of some microbes. There were no signs of diffusion zones around the protein indicating that the applied EMD proteins aggregated on the agar surface and that only microbes in direct contact with the proteins were inhibited in growth. When samples were harvested from inhibition zones and cultured into liquid medium (LB broth with supplements) mono-cultures of the original microbes could be revived suggesting that the active proteins are not microbicidal. All controls tested negative indicating that no unspecific mechanism influenced the results.

TABLE 1

GROWTH (+/−) ON TOP OF TEST SUBSTANCE

| Strains | Serum albumin | Collagen type 1 | Propylene-glyco-lalginateate | EMDO-GAIN® | EMD | EMD heated | EMD fraction A | EMD fraction B | EMD fraction C | EMD fraction H | Hyaluronic acid | Buffer control |
|---|---|---|---|---|---|---|---|---|---|---|---|---|
| *Actinobacillus actinomycetemcomitans* | + | + | + | − | − | − | +/− | + | − | + | + | + |
| *Escherechia coli* | + | + | + | − | − | − | + | + | +/− | + | + | + |
| *Staphylococcus aureus* | + | + | + | − | − | − | + | + | + | + | + | + |
| *Streptococcus mutans* | + | + | + | − | − | − | + | + | + | + | + | + |
| *Bacillus subtilis* | + | + | + | + | + | + | + | + | + | + | + | + |
| *Candida albicans* | + | + | + | + | + | + | + | + | + | + | + | + |

EMD fraction A: mostly amelogenin ~26-20 kDA,
EMD fraction B: ~17-13 kDa proteins,
EMD fraction C: ~10-5 kDa peptides
EMD fraction H: all proteins in EMD above 27 kDa in molecular weight.
+ indicates normal growth of microbes,
− indicates totally inhibited growth of microbes,
+/− indicates some growth inhibition when compared to negative controls.

Example 2

Investigation of the Growth of Microorganisms in the Presence of Enamel Matrix Derivatives and enamel Matrix Proteins The purpose of this example is to demonstrate the inhibitory influence of enamel matrix derivatives and enamel matrix proteins on microbial growth in vitro.

All results in the table is recorded on the second day (aerobic cultures) or after five days (anaerobic cultures) of incubation.

These results show that EMD contained proteins or peptides, when allowed to aggregate on a surface can inhibit growth of certain gram negative rods and some gram positive cocci. Based on the basic behaviour characteristics of EMD proteins (ref. jpc) and since the effect is not microbicidal a reasonable explanation for the observed effect is that protein aggregates form an insoluble barrier that separates the microbes from required growth substrate(s).

Example 3

Effect of EMD on the Rate of Attachment of *Actinomyces viscosus* In Vitro

Introduction

The effect of EMD on the initial attachment of *Actinomyces viscosus*, an oral organism that widely occurs in dental plaque but is commonly not considered as being associated with severe periodontitis, was explored. Although this organism may form aggregates with *Porphyromonas gingivalis* and may thus have an influence on the colonisation of the root surface with potential periodontal pathogens, *Actinomyces* spp are found in relatively large proportions in healthy subgingival sites (these findings corroborate with those of Liljemark et al., *Microbiol. Immunol.* 8, 1993, pp. 5-15, who found that, following periodontal treatment, the proportions of *Actinomyces* spp. was significantly increased. Haffajee et al., *J. Clin. Periodont.* 24, 1997, pp. 767-776, concluded from microbiological counts in subgingival plaque that in subjects with a good response to initial periodontal treatment *A. viscosus* and *T. denticola* were relatively abundant.

Materials

*Actinomyces viscosus* HG85 was provided by Dr. A. J. van Winkelhoff (Dept. of Oral Microbiology, ACTA). EMDOGAIN® was provided by BIORA (Malmö, Sweden). RBS detergent was purchased from Fluka (Fluka Chemie AG, Buchs, Switzerland).

Bacterial Growth and Harvesting

*A. viscosus* was inoculated from blood agar plates in batch culture in Schaedler's broth medium for 24 h at 37° C. This culture was used to inoculate a second culture in Schaedler's broth which was allowed to grow for 16 h. Cells were harvested by centrifugation (5 min at 6500×g) and washed twice with demineralized water. Subsequently, microorganisms were sonicated for 20 sec at 30 W (Vibra Cell model 375, Sonics and Materials Inc., Danbury, Conn., USA) to break bacterial chains and aggregates. Sonicafion was done intermittently while cooling in a bath with ice and water. Cells were counted by using a Bürker-Türker cell counter. Finally, *A. viscosus* was suspended in adhesion buffer (2 mM potassium phosphate, 50 mM potassium chloride and 1 mM calcium chloride, pH 6.8).

Coating of Glass Plates

Glass plates were cleaned thoroughly by sonication in 5% RBS detergent, extensive rinsing with tap water, washing in methanol and finally rinsing with distilled water. This procedure yields a water contact angle of zero degrees. EMD was dissolved in 0.01 M acetic acid in a concentration 7.5 mg/ml. The glass plates were divided into two halves by using teflon marker (DAKO A/S, Glostrup, Denmark). Acetic acid (0.01 M) was applied to one side; 250 µg EMD to the other. Glass plates were air-dried in a flow cabinet for 4-6 h.

Flow Experiment

Figures 3, 3A:
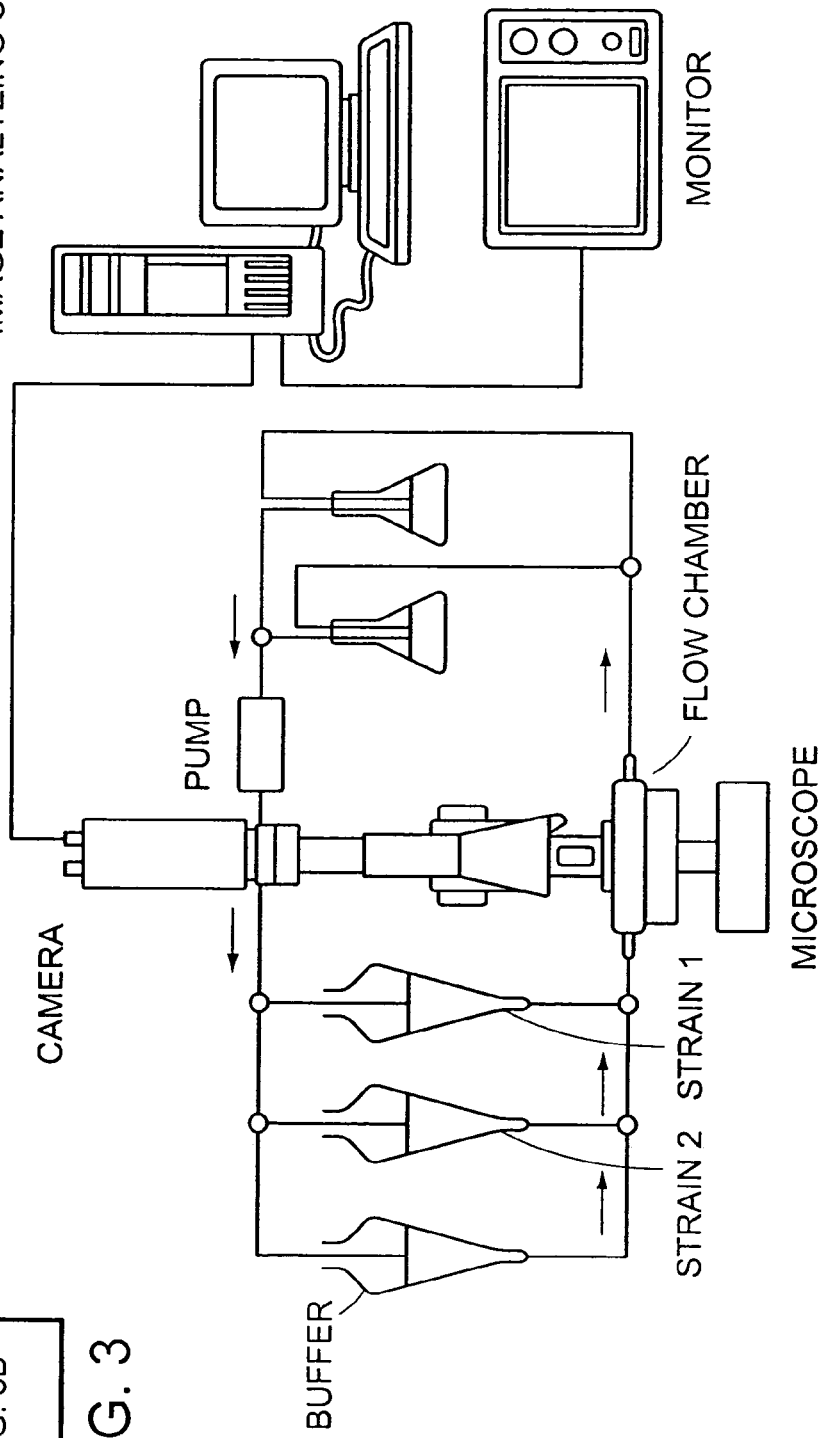
FIG. 3 is a schematic drawing of a flow chamber and computer system used in the flow experiment described in Examples 3 and 4 below.
Figure 3B:
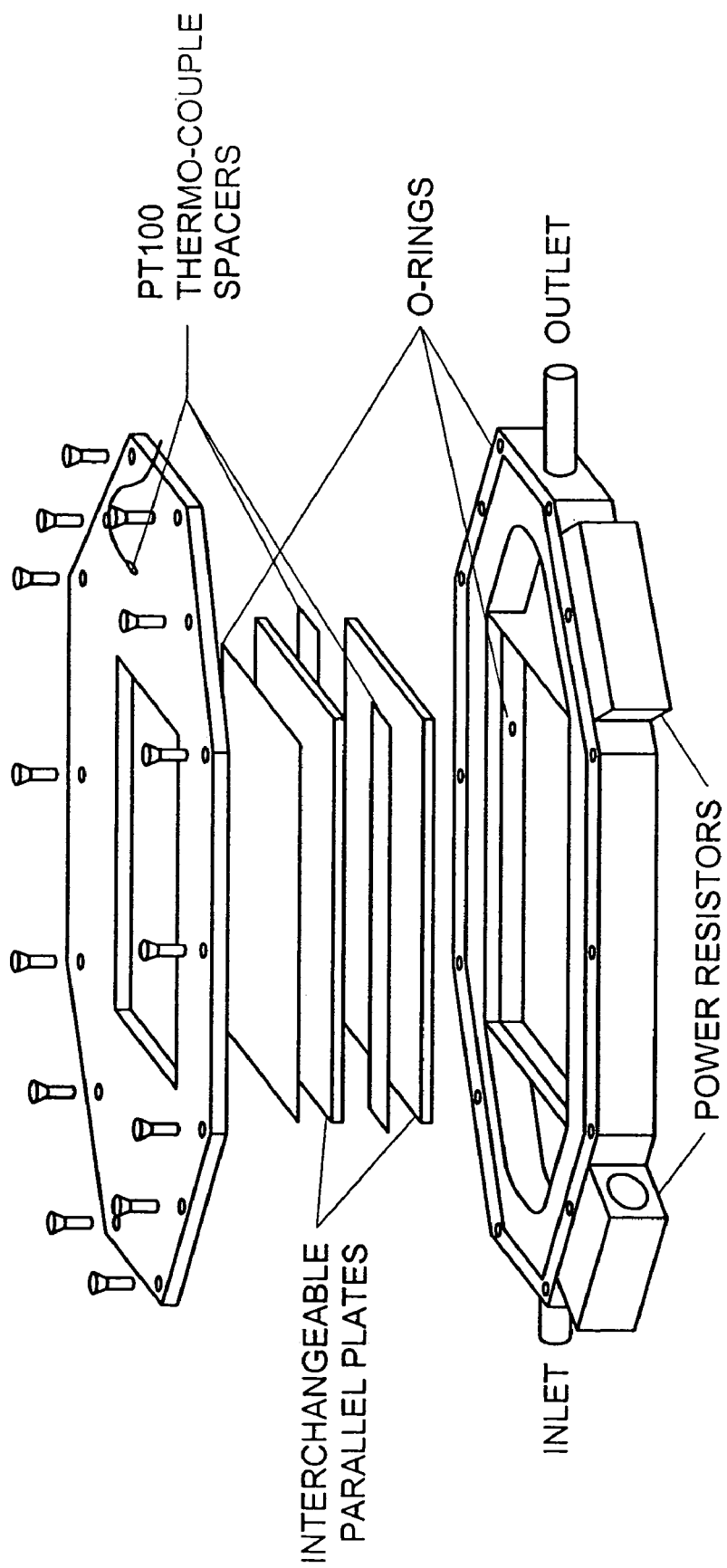

The flow chamber and computer system used in this experiment are shown schematically in FIG. 3. Prior to each experiment, all tubes and the flow chamber as well were filled with adhesion buffer, care being taken that the system did not contain air bubbles. The coated glass plates formed the bottom of the flow chamber. Flow rate was set at 2.5 ml/min (which is comparable with the average flow rate of saliva in humans). The bacterial suspension was circulated through the system for approximately 3-4 h, and the number of bacteria adhering to the substrate was counted. Three independent experiments were carried out. All experiments were performed with $3 \times 10^8$ cells per 250 ml of adhesion buffer. During the experiment, images were taken every 10-15 min at 6 predetermined sites over both control and EMD coated plates. The channel height of the parallel flow chamber was 0.6 mm.

Data Analysis

After counting the adhering cells in all images, data were transformed to bacteria per square centimetre. For each experiment the final number of microorganisms per $cm^2$ was used for statistical analysis (Student's t-test for paired observations using n as the number of experiments).

Results

Figure 4:
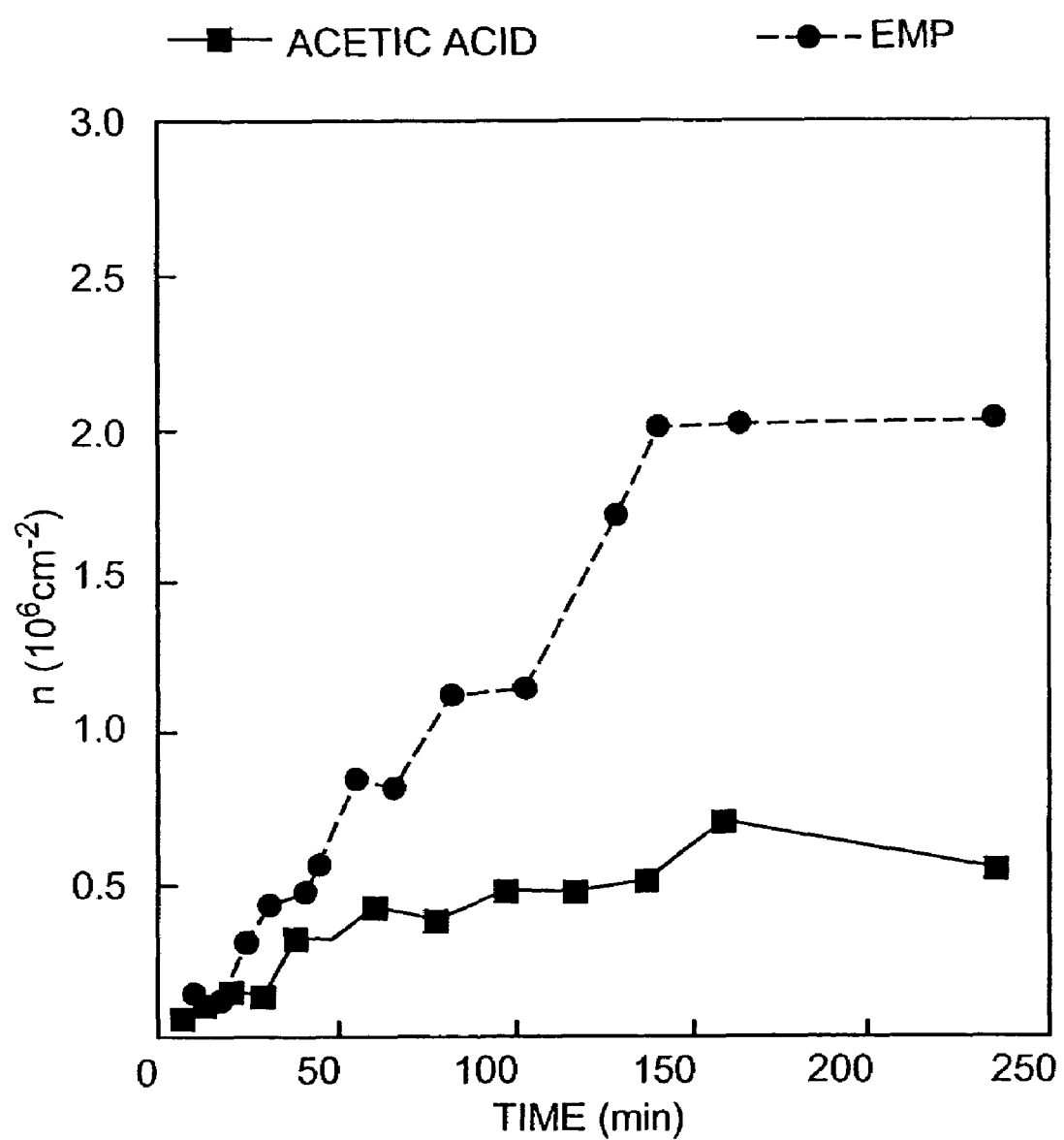
FIGS. 4, 5 and 6 are graphs showing the results of three separate experiments showing the attachment of *Actinomyces viscosus* to glass plates treated with EMD and acetic acid, respectively.

Experiment 1 (FIG. 4) showed a gradual increase of the amount of attached micro-organisms particularly during the first 150 min of flowing. After this time-interval the number of micro-organisms attached to EMD had reached a plateau of $2.0 \times 10^6$ bacteria per $cm^2$ which was about four times higher than on the acetic acid-treated aspect of the glass plate.

Figure 5:
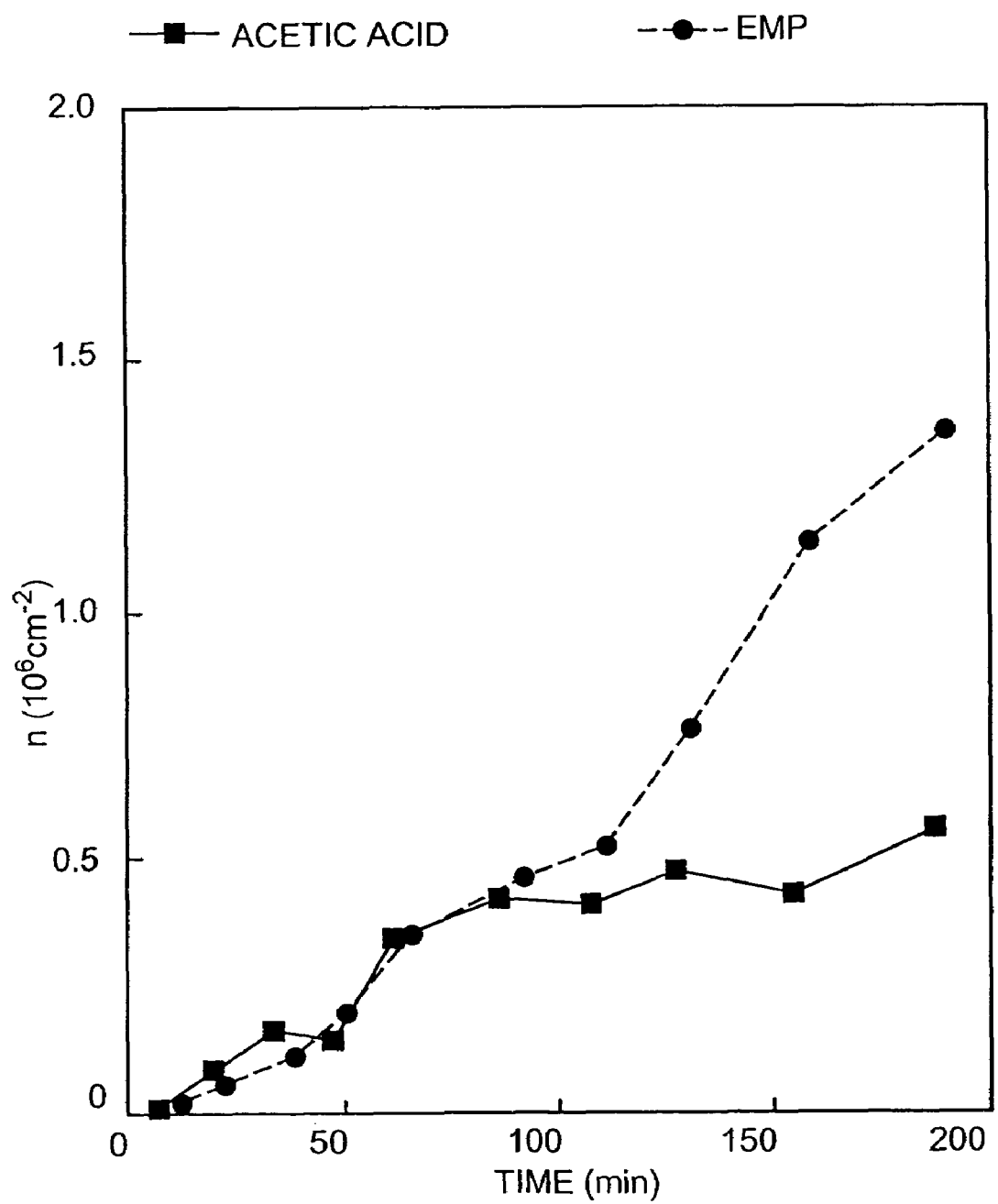

Also in experiment 2 (FIG. 5), EMD quite dramatically stimulated the attachment of *A. viscosus* to the substratum. However, in the beginning of the experiment the effect was less clear. Perhaps this was due to a lower density of organisms used in the flow system. After 90 min the number of bacteria attaching to EMD gradually increased relative to control, reaching a maximum of $1.4 \times 10^6$ per $cm^2$ after 3 h, a threefold increase.

Figure 6:
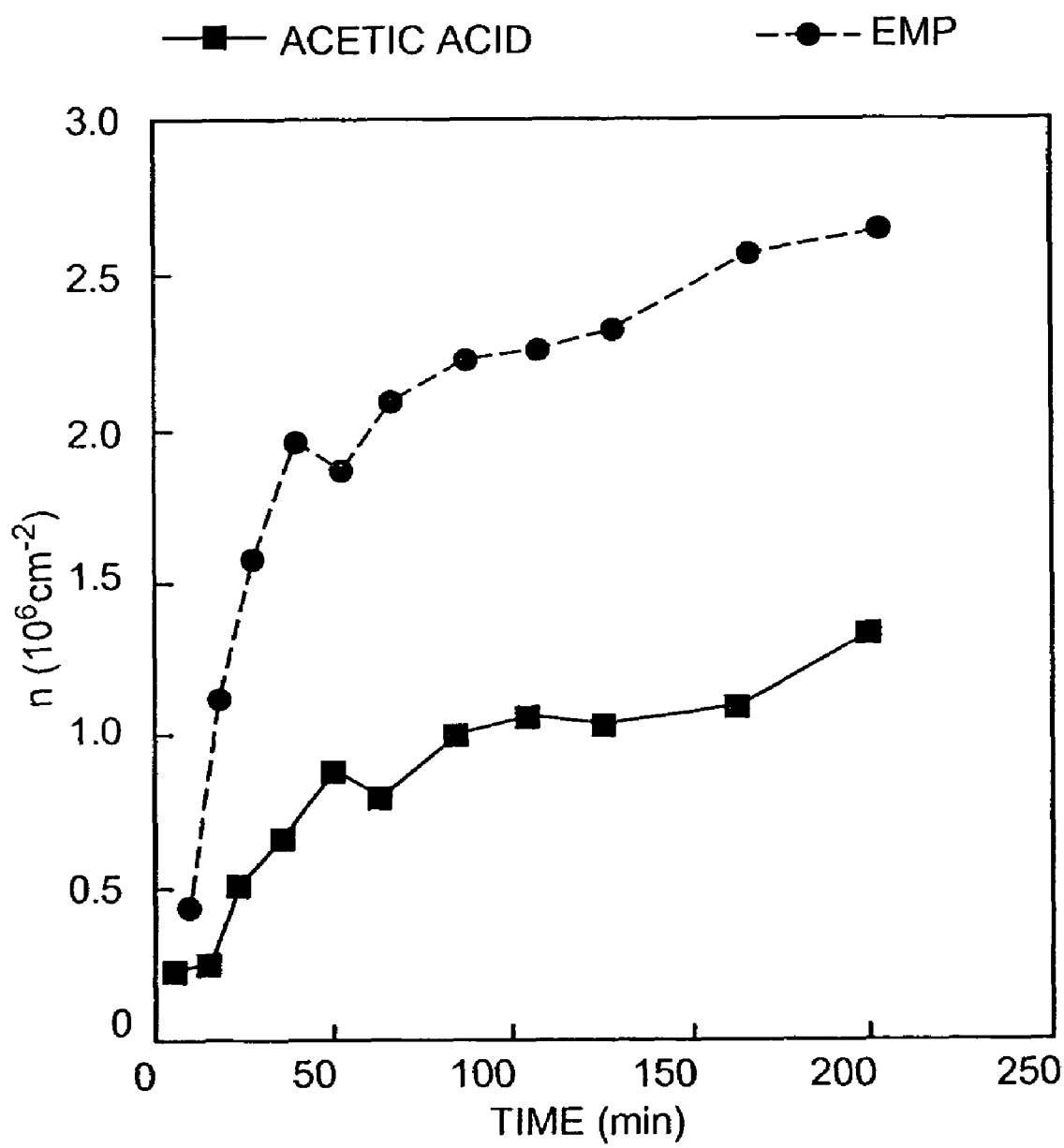

The third experiment (FIG. 6) showed a stimulation of the adherence of *A. viscosus* to the EMD coating already after 5 min of flowing. EMD induced a rapid increase in the number of attached organisms during the first 45 min. Thereafter, the attachment continued progressively. Attachment to the acetic acid-treated side showed a similar pattern, but with for less micro-organisms adhering. After 200 min, attachment to the EMD coating was two times higher than on the acetic acid treated surface.

In the 3 experiments, taken together, the difference proved to be statistically significant ($p<0.05$).

From the results it appears that EMD, used as a coating on a glass surface, has a considerable stimulatory effect in vitro on the attachment of *A. viscosus*. Although it is not yet known which factors are responsible for this enhanced initial attachment, it is assumed that the organism interacts with the proline residues that are richly present in the amelogenin component of the commercially available protein mixture. Bacterial adhesion is often determined by specific protein-peptide and lectin-carbohydrate recognition. It is known that *A. viscosus*, with its type 1 fimbriae, can bind to proline-rich proteins, like salivary Proline-Rich Proteins (PRP's) and type I and III collagens.

Specific interactions between EMD and certain oral micro-organisms might have important consequences for the composition of the biofilm in the oral cavity, since the ecology of the plaque may change. If ecological shifts could be made in the direction of promoting organisms not associated with periodontal disease, application of EMD might result in improvement of the periodontal condition, just by that action. This of course is quite apart from other beneficial effects of EMD.

Example 4

Effect of EMD on the Rate of Attachment of *Streptococcus mutans* In Vitro

Introduction

There is a large body of evidence for a causative role of plaque organisms in the pathogenesis of oral diseases like periodontitis and caries. According to the current model of supragingival plaque formation, *Streptococcus* spp. are thought to be the predominant colonizers of the tooth surface. Subsequently, plaque develops by bacterial growth and by further accretion of other bacterial species. This accretion can occur via bacterium-bacterium binding or may be mediated by salivary molecules. Plaque build-up is also facilitated by the production of extracellular macromolecules. *S. mutans* is now considered to be one of the biofilm species that may warrant closest attention, because of its association with dental caries. Although several gram-positive bacteria (i.e. *S. mutans*) have been shown to cause alveolar bone loss in gnotobiotic animals, these microorganisms do not appear to be major contributors to the ecology of the developing periodontal pocket. Nevertheless, potentially pathogenic microorganisms must be capable of evading both the host defense and immune mechanisms, as well as initiating destruction of the host tissue.

Materials

*Streptococcus mutans* NS was kindly provided by Dr. H. van der Mei (Materia Technica, University of Groningen). EMDOGAIN® was provided by BIORA (Malmö, Sweden). RBS detergent was purchased from Fluka (Fluka Chemie AG, Buchs, Switzerland).

Bacterial Growth and Harvesting

*S. mutans* was inoculated from blood agar plates in batch culture in Todd Hewitt broth medium for 24 h at 37° C. This culture was used to inoculate a second culture in Todd Hewitt broth medium, which was allowed to grow for 16 h. Cells were harvested by centrifugation (5 min at 6500×g) and washed twice with demineralized water. Subsequently, microorganisms were sonicated for 20 sec at 30 W (Vibra Cell model 375, Sonics and Materials Inc., Danbury, Conn., USA) to break bacterial chains and aggregates. Sonicafion was done intermittently while cooling in a bath with ice and water. Cells were counted by using a Bürker-Türker cell counter. Finally, *S. mutans* was suspended in adhesion buffer (2 mM potassium phosphate, 50 mM potassium chloride and 1 mM calcium chloride, pH 6.8).

Coating of Glass Plates

Glass plates were cleaned thoroughly by sonication in 5% RBS detergent, extensive rinsing with tap water, washing in methanol and finally rinsing with distilled water. This procedure yields a water contact angle of zero degrees. EMD was dissolved in 0.01 M acetic acid in a concentration 7.5 mg/ml. The glass plates were divided into two halves by using teflon marker (DAKO A/S, Glostrup, Denmark). Acetic acid (0.01 M) was applied to one side; 250 µg EMD to the other. Glass plates were air-dried in a flow cabinet for 4-6 h.

Flow Experiment

The flow chamber and computer system used in this experiment are shown schematically in FIG. 3. Prior to each experiment, all tubes and the flow chamber as well were filled with adhesion buffer, care being taken that the system did not contain air bubbles. The coated glass plates formed the bottom of the flow chamber. Flow rate was set at 2.5 ml/min (which is comparable with the average flow rate of saliva in humans). The bacterial suspension was circulated through the system for approximately 3-4 h, and the number of bacteria adhering to the substrate was counted. Three independent experiments were carried out. All experiments were performed with $3\times10^8$ cells per 250 ml of adhesion buffer. During the experiment, images were taken every 10-15 min at 6 predetermined sites over both control and EMD coated plates. The channel height of the parallel flow chamber was 0.6 mm.

Data Analysis

After counting the adhering cells in all images, data were transformed to bacteria per square centimetre. For each experiment the final number of microorganisms per $cm^2$ was used for statistical analysis (Student's t-test for paired observations using n as the number of experiments).

Results

Figure 7:
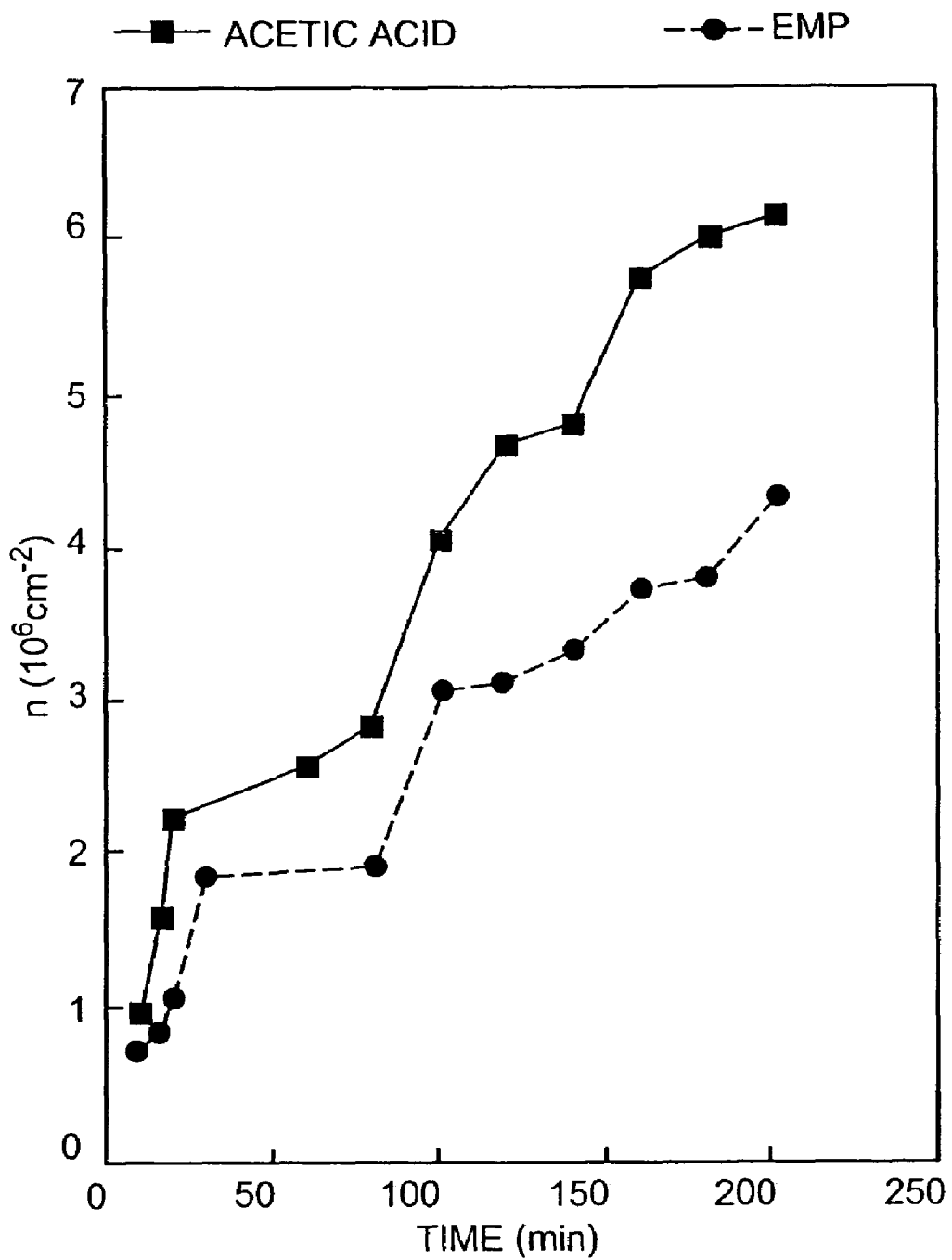
FIGS. 7, 8 and 9 are graphs showing the results of three separate experiments showing the attachment of *Streptococcus mutans* to glass plates treated with EMD and acetic acid, respectively.
Figure 8:
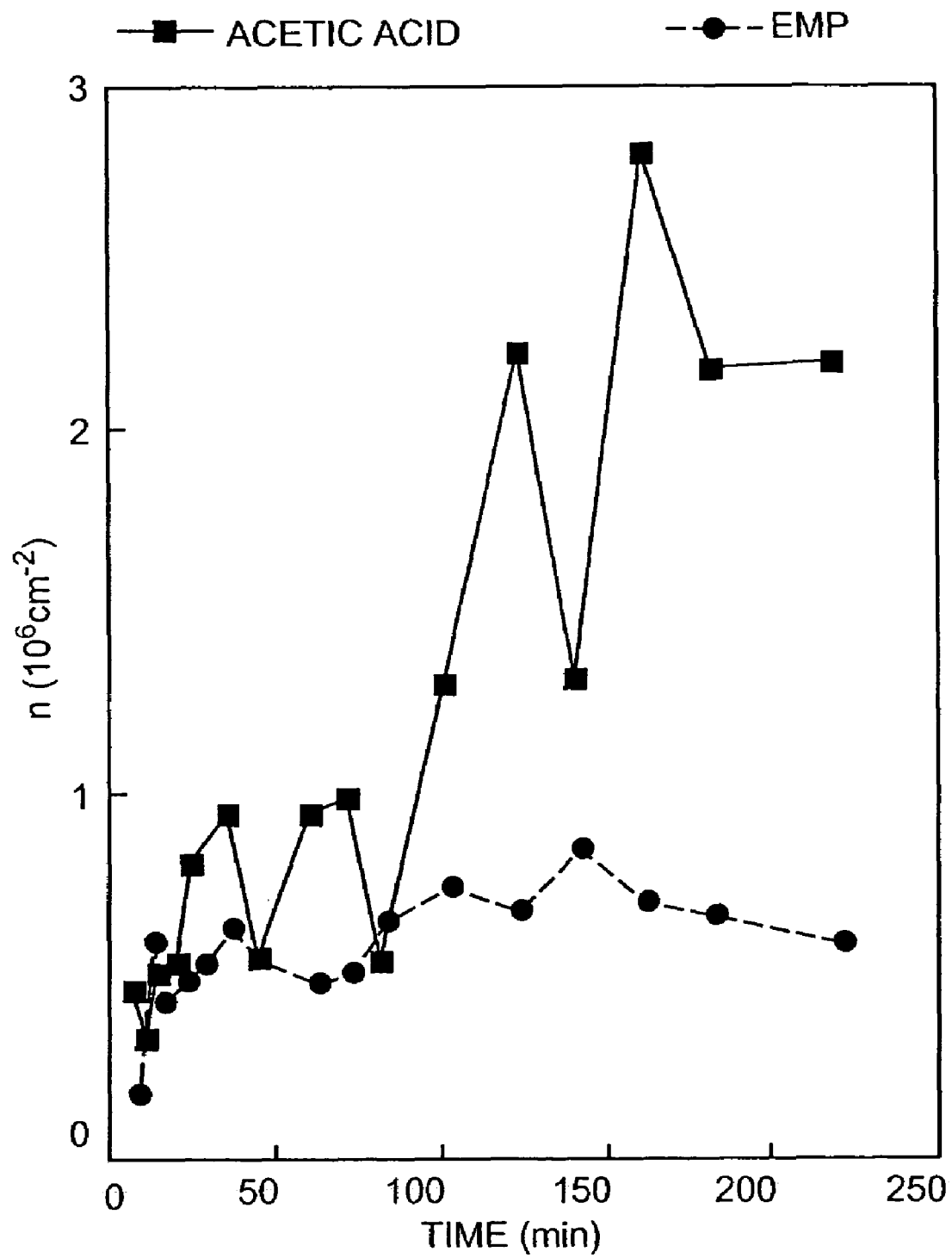
Figure 9:
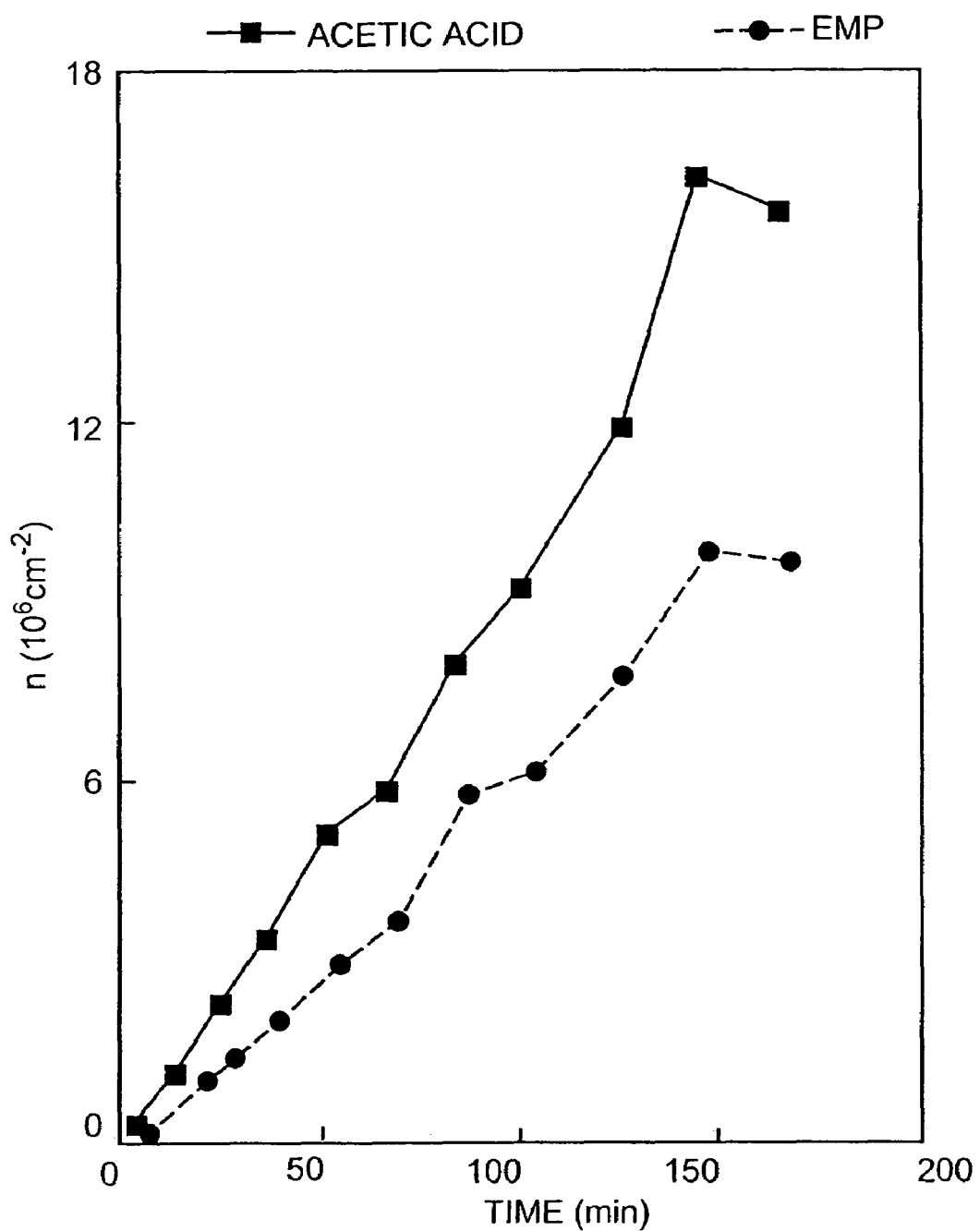
Figure 10A:
FIG. 10A is an X-ray photograph showing postoperative damage following removal of a wisdom tooth.
Figure 10B:
FIG. 10B is an X-ray photograph showing regeneration of periodontal ligament following treatment with EMD, as described in Example 12 below.

In each of the three experiments EMD showed an inhibitory effect on the rate of attachment of *S. mutans* (FIGS. 7, 8, 9; $p<0.05$). Inhibition amounted to approximately 40-70% when compared to acetic acid treated controls.

The first experiment (FIG. 7) showed already after 10 min of flowing an inhibition of the amount of attached *S. mutans* attaching to the EMD coated glass surface. After 3 h attachment was inhibited to about 60% of control.

In the second experiment (FIG. 8) EMP began to inhibit the attachment of *S. mutans* after 1½ h of flowing. The number of *S. mutans* adhering to EMD reached a plateau of 0.5 million per $cm^2$ after about 40 min of flowing. After 3½ h, counts were about 25% compared to controls.

The third experiment (FIG. 9) showed inhibition of attachment of *S. mutans* under the influence of EMD already from the beginning of the flowing procedure. As in experiment 1 inhibition amounted up to 60% of control values after 3 h of flowing.

The present study shows that EMD has a significant inhibitory effect on the adherence of *S. mutans* to glass surfaces. A possible explanation for this inhibition might be the presence of hydrophobic compounds in the EMD mixture. One of the proteins abundantly present in the mixture is amelogenin, a protein that contains, besides an acidic hydrophilic C-terminal sequence, a hydrophobic core containing 100-300 residues enriched in proline, leucine, methionine and glutamine. Saito et al., *Arch. Oral Biol.* 42, 1997, pp. 539-545, found that the adherence of various *S. mutans* strains to an immobilised hydrophobic protein (OAIS) was inhibited. The authors ascribed the effect to the negative charge on the cell surface of the microorganisms (which is the case for *S. mutans*). Other surface characteristics might also be involved in the affected adherence to the substrate. *S. mutans* contains a surface antigen I/II which has an N-terminal part particularly rich in alanine and includes tandem repeats. This region is predicted to be alpha-helical, adopting a coiled-coil conformation, and may account for the cell surface hydrophobicity associated with the expression of antigen I/II.

Example 5

Effect of EMD on Growth of Certain Periopathogens

*Prevotella intermedia* and *Porphyromonas gingivalis* were precultures for 10-16 hours at 37° C. in thioglycolate broth supplemented with 0.5 mg/l of Vitamin K and 5 mg/l hemin in an aerobic atmosphere generated by GasPakPlus envelopes in appropriate jars. When cultures reached an OD$_{600}$ of 0.1-0.2 corresponding to cell densities of $10^6$-$10^7$ cfu (colony forming units) per ml, 100 μl aliquots were drawn and the bacteria were precipitated by centrifugation. The bacteria were resuspended in 100 μl of a freshly prepared mixture of human serum and sterile saline, and the suspensions containing $10^5$-$10^6$ cells were transferred to sterile 1.5 ml Eppendorf tubes and mixed with (i) 100 μl EMD preparation (3 mg EMD in 0.1 ml PGA), (ii) 100 μl PGA vehicle or (iii) 100 μl of the serum/NaCl solution mixture as growth control. 10 μl aliquots for the growth assays were taken after 0, 3, 6 and 24 hours. The aliquots were serially diluted in sterile 0.9% NaCl solution and 10 μl of the dilution steps were plated onto Schaedler agar. Culture conditions were the same as for the precultures. Agar plates were incubated for 3-4 days and cfus and cell densities (cfu/ml) were subsequently calculated. All experiments were repeated six times.

Results (given as cfu/ml in percent of the concentration at time 0).

| 1) Control cultures at different time points | | | | |
|---|---|---|---|---|
| | 0 | 3 h | 6 h | 24 h |
| P. intermedia | 100 | 160 | 25 | 10 |
| P. gingivalis | 100 | 100 | 125 | 150 |

| 2) Cultures in the presence of PGA vehicle at different time points | | | | |
|---|---|---|---|---|
| | 0 | 3 h | 6 h | 24 h |
| P. intermedia | 100 | 140 | 25 | 10 |
| P. gingivalis | 100 | 75 | 50 | 5 |

| 3) Cultures in the presence of EMD at different time points | | | | |
|---|---|---|---|---|
| | 0 | 3 h | 6 h | 24 h |
| P. intermedia | 100 | 40 | 0 | 0 |
| P. gingivalis | 100 | 30 | 0 | 0 |

The cultures were markedly inhibited by the presence of EMD as compared to the controls with vehicle alone or without any addition of EMD.

Example 6

Investigation of Improved Soft Tissue Wound Healing Effect of EMDOGAIN® after Periodontal Surgery The purpose of this example is to show the influence of the enamel matrix derivatives and/or enamel matrix proteins on improved soft tissue wound healing after periodontal surgery.

Experimental defects in the marginal periodontium of more than 50 Macaca monkey teeth were created by removing dental cementum, periodontal membrane and marginal alveolar bone to a cervico-apical distance of approximately 5 mm with a dental burr. Nothing (control) or enamel matrix derivative (obtained from EMDOGAIN® either as the non-reconstituted lyophilized powder or as the reconstituted composition) was then applied to the experimental defects. The concentration of the proteins in the re-constituted composition was about 5-30 mg/ml and the volume applied was in the range of from about 0.1 to about 0.2 ml per defect.

The wound healing was visually evaluated during the following 8 weeks. In defects where EMDOGAIN® was applied there was good healing (no redness nor swelling) and negligible plaque after 2 weeks when the sutures were removed, good healing and little gingivitis after 5 weeks and healing without complications after 8 weeks, when the experiments were terminated. In contrast, the control defects showed inflammations with retractions and abundant plaque after 2 weeks, with severe retractions and gingivitis both after 5 weeks and after 8 weeks.

Example 7

Investigation on the Wound Healing Effect of Enamel Matrix Derivatives and Enamel Matrix Proteins After Periodontal Surgery The purpose of this example is to show the influence of the enamel matrix derivatives and enamel matrix proteins on rapid wound healing in patients after periodontal surgery.

Fifty-five (55) patients needing periodontal surgery were divided into two groups, one obtaining conventional surgery with modified Widman flap technique (20 patients) and another with the same procedure plus application of EMDOGAIN® (35 patients) (concentration was 30 mg protein/ml and about 0.3 ml was applied per tooth). None of the patients received antibiotics at the time of surgery but all were instructed to use aseptic (chlorhexidine) mouthwash daily.

Active questioning of the patients was performed at the time of removal of sutures (1-3 weeks after surgery). While 3 (15%) of the control patients had post-surgical events requiring antibiotics, only one (3%) of the EMDOGAIN® treated patients needed such treatment.

Example 8

Investigation of the Wound Healing Effect of Enamel Matrix Derivatives and Enamel Matrix Proteins after Tooth Extraction The purpose of this example is to show the influence of enamel proteins/enamel matrix derivatives on wound healing after 3rd molar extractions.

Patients aged 30 years or older with symmetrical impacted or semiimpacted mandibular third molars requiring removal had one third molar extracted by the classical method involving raising a vertical flap to perform necessary osteoctomy and sectioning, while the second was extracted and the alveolus was filled with EMDOGAIN® prior to suturing. All patients received antibiotics (3 g Amoxicillin or 1 g Erythromycin) 1-2 hours prior to surgery and were given Ibuprofen (600 mg×3) after surgery. They were then instructed to rinse with Chlorhexidine (0-1%, 10 ml×2) for 4 weeks.

Sutures were removed after 2 weeks. The healing of EMDOGAIN® and control sites was evaluated both by the patient and the dentist. In one centre, 9 patients had contralateral extractions with/without EMDOGAIN®. One patient had slight irritation from sutures at both sites, while another patient had severe pain at the control site only but no problems at the EMDOGAIN® treated site. In a second centre, three patients out of 6 had pain only from the control sites. Finally, in a third centre one patient had a serious event, alveolitis, which was diagnosed at the control site of a patient. The EMDOGAIN® treated site healed without problems. Another patient had slight irritation from sutures at both extraction sites, but only the control site was inflamed and painful and required repeated irrigations with saline and intake of painkillers.

These clinical results indicate that application of EMDOGAIN® in the extraction alveolus after wisdom tooth extraction can ameliorate the healing and reduce the otherwise frequent painful swellings.

Example 9

Investigation of the Effect of Enamel Matrix Derivatives and Enamel Matrix Proteins on the Healing of Alveolitis Sicca The purpose of this example is to show the influence of enamel proteins/enamel matrix derivative on healing of alveolitis sicca (dry socket).

After removal of an infected 35 radix relicta, a male patient, aged 70, experienced severe pain and swelling in relation to the extraction alveola. When examined by his dentist it became clear that he had developed a condition of alveolitits sicca, in which the initial coagulum had disintegrated and the bone wall of the alveola was necrotic. The adjacent bone and soft tissues were inflamed.

The patient had a history of cardiac failure and was treated with the anticoagulant Marevan. As a result of his condition he had reduced peripheral blood circulation. He also smoked regularly several cigarettes a day.

The alveolitis was treated in the traditional way with removal of necrotic bone and induction of new bleeding. Also, gingiva was mobilised and a suture was applied to close the alveola. The patient was then treated with penicillin (apocillin 660 mg, 2 tablets morning and evening for seven days) to fight the infection and also instructed to rinse his mouth twice daily with a chlorhexidine solution. After five days, after ending his antibiotic regime, the patient showed up at the dental clinic still complaining about severe pain. Inspection of the operation area was performed visually and by palpation and probing and showed that the alvolitis persisted and that more necrotic bone was present. X-ray revealed bone destruction and necrosis all the way down to the apical part of the alveola. The operation area was cleaned out once more and the resulting bone lesion was filled with EMDOGAIN® (30 mg/ml, max. 0.5 ml was applied), and a new suture was placed in the gingiva to close the alveola. No additional treatment was instituted, but the patient was told to continue rinsing with chlorhexidine solution. Two days later the patient reported back to the clinic that both the pain and the swelling had gone. Clinical examination and removal of the suture one week after EMDOGAIN® treatment revealed good healing with no signs of necrotic tissues or inflammation and an intact gingiva without redness or swelling covered the wound area. No bleeding or pain when probed and palpated. No foul odour or taste or exudes could be observed. The patient did not report any pain or other symptoms findings.

Example 10

Investigation of the Prophylactic Effect of Enamel Matrix Derivatives and Enamel Matrix Protein on Alveolitis Sicca The purpose of this example is to show the prophylactic effect of enamel matrix derivatives and enamel matrix proteins to counteract alveolitis sicca.

An 82-year old female patient experienced a longitudinal root fracture of tooth 44. This tooth was a pillar in a bridge spanning from tooth 35 to 46, and had undergone endodontic treatment several years earlier. Clinically, the gingival surrounding the tooth was inflamed and there was a gingival pocket all the way to the apex of the tooth on the lingual side. X-ray showed severe local periodontitis of tooth 44.

The patient had good oral hygiene, but due to a heart condition treated with Marevan (anti-coagulant), bleeding from the gingiva was easily provoked by probing. Six months earlier the patient had had her tooth 35 removed surgically due to severe periodontitis. After that operation she experienced a long lasting condition of alveolitis sicca. She was very concerned that the removal of tooth 44 would not cause the same postsurgical complications she had experienced then. She was informed that the combination of her high age, Marevan treatment and infected root and gingival pocket dramatically increased the risk for postoperative complications like alveolitis, but that there was no alternative but to surgically remove the root fragments.

The patient agreed to have tooth 44 removed and, as an experiment, undergo prophylactic treatment with EMDOGAIN® to prevent the development of alveolitits sicca. The patient was anaesthetised with incision and removal of buccal bone to allow removal of the root fragment without loosening the bridge. After removal, the empty alveola was mechanically cleaned and filled with EMDOGAIN® (30 mg/ml, max. 0.5 ml was applied) and the flap was repositioned with one suture. In the same evening the patient reported (by phone) prolonged bleeding from the operation area (Marevan treatment was not stopped prior to surgery) but no other symptoms. When the suture was removed five days after surgery, the operation soft tissue wound had completely healed. The patient did not report any symptoms like pain or swelling after surgery and was generally very pleased with the treatment.

Example 11

Investigation of the Effect of Enamel Matrix Derivatives and Enamel Matrix Proteins on Healing of Post-Traumatic Complications The purpose of this example is to show the influence of enamel proteins/enamel matrix derivative on healing of post-traumatic complications in a patient.

After an accident a patient had the affected upper front teeth ligated in an emergency clinic. The dentist found teeth 11 and 21 avital, teeth 12 and 22 had mesio-incisal fractures class 1 or 11. The marginal gingiva was severely inflamed and adhered poorly to the tooth surfaces. The patient had pain and complained of numbness, swelling and bad taste and smell. There was also evidence of periodontal ligament injury in the apical regions of the teeth 11 and 21. Both central incisors were cleansed and root-filled with freshly mixed $Ca(OH)_2$.

After 4 weeks the wound healing was still judged as unsatisfactory. The condition had evolved into a chronic inflammation and the teeth were regarded as lost. Standard treatment of this condition would be extraction of all four incisors and replacement with a bridge or implants. However, the patient strongly opposed this treatment and as a last effort to save the teeth, a gingival flap surgery was performed on all four affected teeth (11, 12, 21, 22). Two vials of EMDOGAIN® were used (60 mg in 3 ml). At the most 0.2 ml of EMDOGAIN® (30 mg/ml) per tooth was applied with a syringe before the flaps were sutured back with 7 stitches. Four of the sutures were removed 5 days after surgery. There was then a marked improvement in the subjective and clinical conditions. The patient no longer complained of pain, the feeling of numbness was gone and there was no foul smell or taste from the affected area. After 2 weeks the remaining sutures were removed. The gingiva did not show any signs of inflammation and the patient had no complaints. The gingiva was sound and had no signs of inflammation; it was firmly attached to the tooth and/or the alveolar bone, it was pink in colour (not distinct red as observed in inflamed areas) and with normal (not swollen) interdental papilla. Furthermore, a marked improvement was observed as reappearance of the periodontal ligament in the affected parts of the teeth, and depositions of new alveolar bone as visualised by X-ray examination.

Example 12

Healing of Traumatic Wounds on Neighbouring Teeth and Nerves

Case Report

A 39 year old female patient experienced a severe pericoronitis around her lower left wisdom tooth (38). At the public dental clinic the tooth was partially removed, leaving the apical half of the tooth in the jaw following an iatrogenic root fracture. In pain, the patient was referred to an specialist in oral surgery the following day for surgical removal of the root fragment.

Two days after surgery the patient went to see her regular dentist for control. She was swollen on her left side and showed a persistent and complete block of the left mandibular nerve. Clinical examination and X-ray photographs showed that during surgery severe damage by drilling was done to the jaw bone, the apical third of the distal root of tooth 37 and to the mandibular nerve canal (see X-rays, FIG. 1A). Probing pocket depth distal on tooth 37 was 25 mm from top of the tooth crown which was past the apex of the distal root.

In an effort to induce bone and nerve healing and regeneration of the lost periodontal ligament on tooth 37, the operation wound was opened and carefully cleaned out. After debridement with saline the exposed bone, distal root surface of 37 and mandibular nerve was covered with EMDOGAIN® (30 mg/ml, applied in surplus; ca. 1 ml) and the wound was stitched together with three sutures. She was instructed to rinse her mouth with a chlorhexidine solution (Corsodyl®) twice a day for the next five days and a five day prophylactic treatment with penicillin (Ampicillin, 660 mg×4) was initiated.

After ten days the patient was back for control and removal of the sutures. At this time the swelling was gone and soft tissue healing was very good. However, the complete anaesthesia of the mandibular nerve persisted and the patient was informed that the prognosis for a ruptured nerve is, at the best, uncertain. At this point the anaesthesia made it impossible to test the viability of tooth 37. Normally a root damage like the one presented here lead to necrosis of the pulp and ankylosis of the tooth. To prevent these complications endodontic treatment is indicated. However, to see if the experimental treatment could promote a periodontal ligament healing the patient agreed to leave the tooth untreated for the time being. The patient was then scheduled for monthly controls.

Two months after the above control the patient had local hyperesthesia in her left lower lip, a sign of nerve healing. The soft tissue in region 37-38 was perfectly healed without scarring. X-rays also revealed new bone forming in the extraction alveola. Tooth 37 and the surrounding tissue still suffered from anaesthesia.

Four months after treatment the anaesthesia was gone and tooth 37 tested vital, but hypersensitive, by both by temperature sensitivity and electricity tests. X-rays showed that the bone fill into the extraction alveola was significant and there were signs of periodontal regeneration on the distal root of tooth 37.

Five months after initial treatment with EMDOGAIN® the vitality of tooth 37 tested normal. At this time a complete regeneration of a functional periodontal ligament was evident on the X-rays (FIG. 1B) and newly formed alveolar bone of normal appearance had filled the bone defects and extraction alveola. There were no signs of ankylosis. Pocket probing depth distal on tooth 37 was now only 10 mm which was approx. 1 mm below the cementoenamel junction. After this control the patient was dismissed as completely healed and scheduled for ordinary recalls at one year intervals.

Comments:

Complete and rapid healing of traumatic wounds on neighbouring teeth and nerves after surgical removal of wisdom teeth are rare. Usually complications as severe as those reported above ends with the complete removal of the damaged tooth, or at least in endodontic removal of the tooth pulp and root filling followed by bone healing with ankylosis. A ruptured nerve normally takes 8 to 12 months to heal, if at all, and often some regions with paresthesia persists for several years. The rapid and good quality of the above reported healing is very unusual and should be regarded a sign for the wound healing capacity of EMDOGAIN®.

X-Rays:

A: Patient two days after removal of tooth 38. Note the big defect distal on tooth 37 and the involvement of the mandibular canal. Also the alveolar bone distobuccal on tooth 37 was removed during surgery.

B: Patient five months after surgery. Note sign of complete functional periodontal ligament (lamina dura) in defect on distal part of root on tooth 37. There are no signs of ankylosis. The outline of the mandibular canal can now be seen and the extraction alveola is completely filled with bone. Also note the new distobuccal alveolar bone forming around tooth 37.

Example 13

Investigation of the Effect of Enamel Matrix Derivatives and Enamel Matrix Proteins on Healing of Ulcus Cruris (Venous Ulcer)

Patient 1

The patient was male, born in 1926 and had a disease history of repeated thrombosis with bad post-thrombotic syndrome and recurrent venous ulcers. He was treated systemically with anticoagulant coumarin derivatives, and the ulcers were treated locally with Crupodex (dextran monomer) BIOGAL and 3% boric acid solution.

At the time of initialization of treatment with EMDOGAIN® he had a venous ulcer having an oval size of 5×4 cm and a depth of 0.5 mm which was in the stage of granulation with very bad epithelization.

The wound was disinfected with 3% $H_2O_2$, and 500 µl of EMDOGAIN® was applied dropwise and spread equally by means of a sterile stick. The EMDOGAIN® was left for 10 minutes in the air and then the wound was covered with Inadine (Johnson & Johnson) Rayon dressing impregnated with 10% Povidone iodine ointment.

After 5 days, epithelization in the proximal part of the ulcer had taken place and the ulcer was decreased by 1.8×2.2 cm, and there was no side reaction (inflammation). No EMDOGAIN® was applied. After 12 days further epithelization in the proximal part and new epithelization in the lateral part had taken place in an area of about 2×2 cm. Almost half of the ulcer had healed. 400 µl of EMDOGAIN® was applied.

After 19 days further epithelization in the proximal and lateral parts of the ulcer had taken place, but not in the distal part where the ulcer was rather deep (about 1 mm). More than half of the ulcer had healed. 300 µl of EMDOGAIN® was applied. Since the initiation of the treatment with EMDOGAIN® the patient did not feel any pain in the ulcer, in contrast to what he did before the initiation of the treatment. EMDOGAIN® was then applied once a week until day 40 (at 200 µl), and the ulcer was considered fully healed after 47 days.

Patient 2

The patient was female, born in 1949 and had varices, chronic venous insufficiency, and recurrent venous ulcers. She had polyvalent allergy towards pharmaceuticals (drugs, medicaments), as well as excema varicosum. She had previously been treated locally with Otosporin drops (polymyxin B sulphate+neomycin sulphate+hydrocortisone) and a hydrocortisone compress.

At the time of initialization of treatment with EMDOGAIN® her venous ulcer was 1 cm in diameter and 2 mm deep. 300 µl of EMDOGAIN® was applied.

After 5 days, the epithelization was 2 mm around the wound (circumferentially) and there was no side reaction (inflammation). No EMDOGAIN® was applied. After 12 days the size of the ulcer had diminished to about 2 mm in diameter, 100 µl of EMDOGAIN® was applied.

After 19 days the ulcer was still about 2 mm in diameter, but the bottom was nicely granulated and the ulcer was not so deep (about 0,2 mm). 100 µl of EMDOGAIN® was applied.

The same patient had another ulcer on the other leg about 0.3×1 cm. 200 µl of EMDOGAIN® was applied.

After 7 days, new epithelization was present and nice granulation at the bottom and the size had diminished to about 0.2×0.5 cm.

100 µl of EMDOGAIN® was then applied to each ulcer once a week until day 40, and the ulcers were considered fully healed after 47 days. No allergic reactions to EMDOGAIN® were observed.

Another ulcer had formed at the same leg having a size of about 0.5×0.3 cm to which 100 µl of EMDOGAIN® was applied.

Patient 3

The patient was female, born in 1929 and had deep venous thrombosis after erysipelas, and at the time of initialization of treatment with EMDOGAIN® she had a very large ulcus cruris having a size of about 15×19 cm in the state of progression proximally which ulcer was considered almost hopeless after various treatments. 700 µl of EMDOGAIN® was applied in an area about 3 cm from the upper margin.

After 7 days, no epithelization was present but the treated area was more transparent (more structure-like) with small scattered areas of granulation and there was no pain in this area and no signs of progression. 700 µl of EMDOGAIN® was applied to the same area.

After 4 weeks, the patient developed an infection, believed to be caused by *Pseudomonas*, in the distal part of the ulcer not treated with EMDOGAIN®. 700 µl of EMDOGAIN® was applied. The infection had disappeared after 7 days.

Patient 4

The patient was female, born in 1947 and had varices with superficial thrombophlebitis after erysipelas, and at the time of initialization of treatment with EMDOGAIN® she had an ulcus cruris having a size of about 2×0.8 cm with clean but not granulating bottom. 300 µl of EMDOGAIN® was applied.

After 7 days, the size of the ulcer had diminished to about 0.7×0,3 cm and epithelization was present all around and granulation at the bottom. 200 µl of EMDOGAIN® was applied, followed by 100 µl of EMDOGAIN® once a week for five weeks. The ulcer was considered fully healed after five weeks.

Example 14

EMDOGAIN® as an adjunct to non-surgical periodontal treatment at flat surface sites.

Objective

The objective of the investigation was to evaluate if application of EMDOGAIN® can improve the healing result of non-surgical periodontal treatment. The specific aim of this study was to evaluate the effect at flat surface sites.

Study Design

The study was conducted as an intra-individual longitudinal test of 6 months duration. The study has a double-blinded, split-mouth, placebo-controlled and randomized design.

Subjects 14 patients referred to the Clinic of Periodontics, Department of Periodontology, Göteborg University, for treatment of moderately advanced periodontal disease.

Criteria for Inclusion
  At least 3 flat tooth surface sites in each of 2 contralateral quadrants with probing pocket depth of ≧5 mm, and at least one pair of sites with a probing depth of ≧6 mm
  Selected teeth must have a vital pulp as determined by thermal or electric stimulation or, if subjected to root canal treatment, be asymptomatic and without technical remars.

Treatment

After a baseline examination, all patients were given a case presentation and instructions in proper supragingival plaque control measures. Scaling and root planing were performed.

When bleeding from the pockets had ceased, 24% EDTA gel (obtained from Biora AB, Sweden) was applied in the pockets for 2 minutes. The pockets were then carefully irrigated with saline followed by application of either the test (EMDOGAIN®) or control substance (PGA gel).

Assessments

Baseline examination, 1-, 2-, 3-, 8- and 24-week follow-up examinations included the variables:
1. Oral hygiene status—presence/absence of plaque
2. Gingival condition—(Gingival Index; Löe 1967)
3. Probing pocket depth 4. Probing attachment level
5. Bleeding on probing—presence/absence (15 seconds)
6. Dentine hypersensitivity—following airblast stimulus (yes/no)
7. Degree of discomfort—recorded at the 1-, 2- and 3-week follow-up examinations using a 10 cm <<Visual Analogue Scale (VAS).

PLAQUE; mean (sd)

|  | CONTROL | EMDOGAIN ® |
|---|---|---|
| Baseline | 0.10 (0.30) | 0.19 (0.40) |
| 1 week | 0.08 (0.27) | 0.05 (0.22) |
| 2 weeks | 0.05 (0.22) | 0.02 (0.15) |
| 3 weeks | 0.05 (0.22) | 0.10 (0.30) |
| 6 weeks | 0.14 (0.35) | 0.19 (0.40) |
| 26 weeks | 0.12 (0.33) | 0.07 (0.34) |

Gingival Index; Mean (sd)

|  | CONTROL | EMDOGAIN ® |
|---|---|---|
| Baseline | 1.40 (0.50) | 1.40 (0.50) |
| 1 week | 1.00 (0.32) | 0.87 (0.52) |
| 2 weeks | 0.83 (0.44) | 0.74 (0.45) |
| 3 weeks | 0.69 (0.60) | 0.60 (0.50) |
| 6 weeks | 0.67 (0.53) | 0.64 (0.58) |
| 26 weeks | 0.62 (0.54) | 0.62 (0.49) |

Bleeding on Probing; %

|  | CONTROL | EMDOGAIN ® |
|---|---|---|
| Baseline | 100 | 100 |
| 1 week | 67 | 44 |
| 2 weeks | 43 | 33 |
| 3 weeks | 29 | 26 |
| 6 weeks | 33 | 31 |
| 26 weeks | 19 | 24 |

Patients' Subjective Evaluation; VAS Score

|  | Week 1 | |
|---|---|---|
| VAS score | CONTROL | EMDOGAIN ® |
| 0-20 | 8% | 0% |
| 21-40 | 15% | 8% |
| 41-60 | 31% | 30% |
| 61-80 | 8% | 0% |
| 81-100 | 38% | 62% |

|  | Week 3 | |
|---|---|---|
| VAS score | CONTROL | EMDOGAIN ® |
| 0-20 | 14% | 7% |
| 21-40 | 0% | 7% |
| 41-60 | 3% | 0% |
| 61-80 | 21% | 22% |
| 81-100 | 57% | 64% |

Conclusion

Patients had less postoperative problems, less bleeding, less plaque and an improved gingival index. These results support the wound healing effect of EMDOGAIN®.

Example 15

Pilot Wound Healing Study in Pigs

Introduction

Objective

The objective of this pilot study is to evaluate the healing process of split-thickness wounds in pigs, and to evaluate the effect of EMD on these wounds.

Reason for the Choice of Animal Species

The pig is selected as the test model because this species has proven to be a good model for assessment of wound healing in humans.

Materials and Methods

Animals

The experiment will be performed in 4 female SPF pigs (crossbreed of Danish country, Yorkshire and Duroc). At start of the acclimatisation period the body weight of the animals will be about 35 kg.

An acclimatisation period of one week will be allowed during which the animals will be observed daily in order to reject an animal presenting a poor condition. All observations will be recorded.

Housing

The study will take place in an animal room provided with filtered air at a temperature of 21° C.±3° C., relative humidity of 55%±15% and air change 10 times/hour. The room will be illuminated to give a cycle of 12 hours light and 12 hours darkness. Light will be on from 06 to 18 h.

The animals will be housed individually in pens.

Bedding

The bedding will be softwood sawdust "LIGNOCEL H ¾" from Hahn & Co, D-24796 Bredenbek-Kronsburg. Regular analyses for relevant possible contaminants are performed.

Diet

A commercially available pig diet, "Altromin 9033" from Chr. Petersen A/S, DK-4100 Ringsted will be offered (about 800 g twice daily). Analyses for major nutritive components and relevant possible contaminants are performed regularly.

Drinking Water

Twice daily the animals will be offered domestic quality drinking water. Analyses for relevant possible contaminants axe performed regularly.

Wounding

The wounds will be established on day 1. The animals will be anaesthetised with Stresnil® Vet. Janssen, Belgium (40 mg azaperone/ml, 1 ml/10 kg), and Atropin DAK, Denmark (1 mg atropine/ml, 0.5 ml/10 kg), given as a single intramuscular injection followed by i.v. injection of Hypnodil® Janssen, Belgium (50 mg metomidate/ml, about 2 ml).

An area dorso-laterally on either side of the back of the animal will be shaved, washed with soap and water, disinfected with 70% ethanol which will be rinsed off with sterile saline, and finally dried with sterile gauze.

Eight split-thickness wounds (25×25×0.4 mm) will be made on the prepared area, 4 on each side of the spine, using an ACCU-Dermatom (GA 630, Aesculap®). The wounds will be numbered 1 (most cranial) to 4 (most caudal) on the left side on the animal, and 5 (most cranial) to 8 (most caudal) on the right side of the animal.

Coagulated blood will be removed with sterile gauze.

Just before surgery, about 8 hours after termination of surgery, and whenever necessary thereafter the animals will be given an intramuscular injection of Anorfin®, A/S GEA, Denmark (0.3 mg buprenorphine/ml, 0.04 ml/kg).

Dosing

After wounding the wounds will be treated as follows:

| Localisation | Animal No. | | | |
| --- | --- | --- | --- | --- |
| | 1 | | 2 | |
| | Left | Right | Left | Right |
| Cranial | A | | | B |
| | B | A | | |
| | | B | A | |
| Caudal | | | B | A |

| Localisation | Animal No. | | | |
| --- | --- | --- | --- | --- |
| | 3 | | 4 | |
| | Left | Right | Left | Right |
| Cranial | A | | | B |
| | B | A | | |
| | | B | A | |
| Caudal | | | B | A |

A = control
B = EMD

At about 15 minutes before dosing, the EMD formulation will be prepared according to instructions given by the manufacturer. The EMD formulation will be used within 2 hours after preparation. For the wounds of treatment B, EMD will be applied as a thin layer to the wound surface. One vial of EMD will be used per 4 wounds.

Wound Dressing

The wounds will be dressed with Tegaderm®. The dressings will be covered with a gauze bandage fixed by Fixomul®. The dressings, the gauze and the Fixomul® will be retained by a netlike body-stocking. Bend-a-rete® (Tesval, Italy), The dressings will be observed on a daily basis.

The dressings will be changed on day 2 (all animals) and 3 (animal Nos. 3 and 4).

Prior to each changing the animals will be anaesthetised with an intramuscular injection in the neck (1.0 ml/10 kg body weight) of a mixture of Zoletil 50®Vet., Virbac, France (125 mg tiletamine and 125 mg zolazepam in 5 ml solvent, 5 ml) Rompun®Vet., Bayer, Germany (20 mg xylazine/ml, 6.5 ml) and Methadon® DAK, Nycomed DAK, Denmark (10 mg methadon/ml, 2.5 ml).

Observation of Wounds

Each wound will be observed and photographed on day 2 (all animals), 3 (all animals) and 4 (animal Nos. 3 and 4). The grade of exudation and inflammation will be evaluated. The appearance of the grafted epidermis will be described in detail.

Clinical Signs

All visible signs of ill health and any behavioural changes will be recorded daily. Any deviation from normal will be recorded with respect to time of onset, duration and intensity.

Body Weight

The animals will be weighed on arrival, on the day of wounding and at termination of the study.

Terminal Observations

On day 3 (about 56 hours after wounding), animal Nos. 1 and 2 will be killed by a cut on the subclavian vein and artery after stunning with a bolt pistol.

On day 4 (about 72 hours after wounding), animal Nos. 3 and 4 will be killed by a cut on the subclavian vein and artery after stunning with a bolt pistol.

Tissue Sampling

Each wound will he cut free as a block separated from skeletal muscle tissue. If any adherence to the underlying skeletal muscle occurs, part of the muscle will be included in the material for fixation. Each block will be fixed in phosphate buffered neutral 4% formaldehyde.

Histological Preparation

After fixation four representative samples from all wounds will be embedded in paraffin, cut at a nominal thickness of 5 µm and stained with haematoxylin and eosin. After staining the slides will be observed under the light microscope using a grid. This allows for measurements of the total length of the wound and length of the epithelialised surface. This ratio will be expressed in percentage of wound covered by epithelial cells per slide. The mean values from each wound will be taken, after which the group mean values will be calculated.

Statistics

Data will be processed to give group mean values and standard deviations where appropriate. Possible outliers will be identified, too. Thereafter each continuous variable will be tested for homogeneity of variance with Bartlett's test. If the variance is homogeneous, analysis of variance will be carried out for the variable. If any significant differences are detected, possible intergroup differences will be assessed with Dunnett's test. If the variance is heterogeneous, each variable will be tested for normality by the Shapiro-Wilk method. In case of normal distribution, possible intergroup differences will be identified with Student's t-test, Otherwise the possible intergroup differences will be assessed by Kruskal-Wallis's test. If any significant intergroup differences are detected, the subsequent identification of the groups will be carried out with Wilcoxon Rank-Surn test.

The statistical analyses will be made with SAS® procedures (version 6.12) described in "SAS/STAT® User's Guide, Version 6, Fourth Edition, Vol. 1+2", 1989, SAS Institute Inc., Cary, N.C. 27513, USA.

The invention claimed is:

1. A method of treating a local inflammatory condition of skin or mucosa, the method comprising topically administering to a mammal in need thereof a therapeutically effective amount of an active enamel substance.

2. The method according to claim 1, wherein the active enamel substance is selected from the group consisting of enamelins, amelogenins, non-amelogenins, proline-rich non-amelogenins, amelins, tuftelins, and mixtures thereof.

3. The method according to claim 2, wherein said amelin is ameloblastin or sheathlin.

4. The method according to claim 1, wherein the active enamel substance has a molecular weight of at the most about 120 kDa, as determined by SDS Page electrophoresis.

5. The method according to claim 4, wherein the active enamel substance has a molecular weight of at the most about 100 kDa.

6. The method according to claim 4, wherein the active enamel substance has a molecular weight of at the most about 90 kDa.

7. The method according to claim 4, wherein the active enamel substance has a molecular weight of at the most about 80 kDa.

8. The method according to claim 4, wherein the active enamel substance has a molecular weight of at the most about 70 kDa.

9. The method according to claim 4, wherein the active enamel substance has a molecular weight of at the most about 60 kDa.

10. The method according to claim 1, wherein the amount of active enamel substance applied is an amount of total protein per cm$^2$ corresponding to from about 0.01 mg/cm$^2$ to about 20 mg/cm$^2$.

11. The method according to claim 10, wherein the amount of active enamel substance is from about 0.1 mg/cm$^2$ to about 15 mg/cm$^2$.

12. The method according to claim 1, wherein the active enamel substance comprises a peptide comprising at least one sequence element selected from the group consisting of Asp-Gly-Glu-Ala (residues 370-373 of SEQ ID NO.: 1), Val-Thr-Lys-Gly (residues 277-280 of SEQ ID NO.: 1), Glu-Lys-Gly-Glu (residues 282-285 of SEQ ID NO.: 1), and Asp-Lys-Gly-Glu (residues 298-301 of SEQ ID NO.: 1).

13. The method according to claim 12, wherein the active enamel substance further comprises an amino acid sequence comprising a consecutive string of 20 amino acids at least 80% identical with a string of amino acids of the same length obtained from a polypeptide comprising SEQ ID NO. 1, amino acids 1 to 103 of SEQ ID NO. 1, or amino acids 6-324 of SEQ ID NO. 2.

14. The method according to claim 1, wherein the local inflammation is of the oral cavity.

15. The method according to claim 1, wherein the mucosa is selected from oral, buccal, nasal, aural, rectal and vaginal mucosa.

16. The method according to claim 1, wherein the active enamel substance is provided on or in a bandage, dressing, drench, patch, sheet, plaster, pad, soap, stick, sponge, transdermal delivery system, or denture.

17. The method according to claim 1, wherein the active enamel substance is provided in a delivery device, spray, aerosol, shampoo, or enema.

18. The method according to claim 1, wherein the active enamel substance is provided as an implant or a coating of the implant.

* * * * *

UNITED STATES PATENT AND TRADEMARK OFFICE
CERTIFICATE OF CORRECTION

PATENT NO. : 7,294,352 B2
APPLICATION NO. : 10/698618
DATED : November 13, 2007
INVENTOR(S) : Gestrelius et al.

It is certified that error appears in the above-identified patent and that said Letters Patent is hereby corrected as shown below:

Column 12, line 58 should read:
   --...consisting of the tetrapeptides DGEA (Asp-Gly-Glu-Ala)...--

Signed and Sealed this

Twenty-ninth Day of April, 2008

JON W. DUDAS
*Director of the United States Patent and Trademark Office*

SEQUENCE LISTING

<160> NUMBER OF SEQ ID NOS: 2

<210> SEQ ID NO 1
<211> LENGTH: 407
<212> TYPE: PRT
<213> ORGANISM: Rattus sp.

<400> SEQUENCE: 1

```
Met Ser Ala Ser Lys Ile Pro Leu Phe Lys Met Lys Gly Leu Leu Leu
  1               5                  10                  15

Phe Leu Ser Leu Val Lys Met Ser Leu Ala Val Pro Ala Phe Pro Gln
             20                  25                  30

Arg Pro Gly Gly Gln Gly Met Ala Pro Pro Gly Met Ala Ser Leu Ser
         35                  40                  45

Leu Glu Thr Met Arg Gln Leu Gly Ser Leu Gln Gly Leu Asn Ala Leu
     50                  55                  60

Ser Gln Tyr Ser Arg Leu Gly Phe Gly Lys Ala Leu Asn Ser Leu Trp
 65                  70                  75                  80

Leu His Gly Leu Leu Pro Pro His Asn Ser Phe Pro Trp Ile Gly Pro
                 85                  90                  95

Arg Glu His Glu Thr Gln Gln Pro Ser Leu Gln Pro His Gln Pro Gly
            100                 105                 110

Leu Lys Pro Phe Leu Gln Pro Thr Ala Ala Thr Gly Val Gln Val Thr
        115                 120                 125

Pro Gln Lys Pro Gly Pro His Pro Pro Met His Pro Gly Gln Leu Pro
    130                 135                 140

Leu Gln Glu Gly Glu Leu Ile Ala Pro Asp Glu Pro Gln Val Ala Pro
145                 150                 155                 160

Ser Glu Asn Pro Pro Thr Pro Glu Val Pro Ile Met Asp Phe Gly Asp
                165                 170                 175

Pro Gln Phe Pro Thr Val Phe Gln Ile Ala His Ser Leu Ser Arg Gly
            180                 185                 190

Pro Met Ala His Asn Lys Val Pro Thr Phe Tyr Pro Gly Met Phe Tyr
        195                 200                 205

Met Ser Tyr Gly Ala Asn Gln Leu Asn Ala Pro Gly Arg Ile Gly Phe
    210                 215                 220

Met Ser Ser Glu Glu Met Pro Gly Glu Arg Gly Ser Pro Met Gly Tyr
225                 230                 235                 240

Gly Thr Leu Phe Pro Gly Tyr Gly Gly Phe Arg Gln Thr Leu Arg Gly
                245                 250                 255

Leu Asn Gln Asn Ser Pro Lys Gly Gly Asp Phe Thr Val Glu Val Asp
            260                 265                 270

Ser Pro Val Ser Val Thr Lys Gly Pro Glu Lys Gly Glu Gly Pro Glu
        275                 280                 285

Gly Ser Pro Leu Gln Glu Pro Ser Pro Asp Lys Gly Glu Asn Pro Ala
    290                 295                 300

Leu Leu Ser Gln Ile Ala Pro Gly Ala His Ala Gly Leu Leu Ala Phe
305                 310                 315                 320

Pro Asn Asp His Ile Pro Asn Met Ala Arg Gly Pro Ala Gly Gln Arg
                325                 330                 335

Leu Leu Gly Val Thr Pro Ala Ala Ala Asp Pro Leu Ile Thr Pro Glu
            340                 345                 350

Leu Ala Glu Val Tyr Glu Thr Tyr Gly Ala Asp Val Thr Thr Pro Leu
```

-continued

```
                355                 360                 365
Gly Asp Gly Glu Ala Thr Met Asp Ile Thr Met Ser Pro Asp Thr Gln
    370                 375                 380

Gln Pro Pro Met Pro Gly Asn Lys Val His Gln Pro Gln Val His Asn
385                 390                 395                 400

Ala Trp Arg Phe Gln Glu Pro
                405

<210> SEQ ID NO 2
<211> LENGTH: 324
<212> TYPE: PRT
<213> ORGANISM: Rattus sp.

<400> SEQUENCE: 2

Met Lys Pro Asn Ser Met Glu Asn Ser Leu Pro Val His Pro Pro Pro
1               5                   10                  15

Leu Pro Ser Gln Pro Ser Leu Gln Pro His Gln Pro Gly Leu Lys Pro
            20                  25                  30

Phe Leu Gln Pro Thr Ala Ala Thr Gly Val Gln Val Thr Pro Gln Lys
        35                  40                  45

Pro Gly Pro His Pro Pro Met His Pro Gly Gln Leu Pro Leu Gln Glu
    50                  55                  60

Gly Glu Leu Ile Ala Pro Asp Glu Pro Gln Val Ala Pro Ser Glu Asn
65                  70                  75                  80

Pro Pro Thr Pro Glu Val Pro Ile Met Asp Phe Gly Asp Pro Gln Phe
                85                  90                  95

Pro Thr Val Phe Gln Ile Ala His Ser Leu Ser Arg Gly Pro Met Ala
            100                 105                 110

His Asn Lys Val Pro Thr Phe Tyr Pro Gly Met Phe Tyr Met Ser Tyr
        115                 120                 125

Gly Ala Asn Gln Leu Asn Ala Pro Gly Arg Ile Gly Phe Met Ser Ser
    130                 135                 140

Glu Glu Met Pro Gly Glu Arg Gly Ser Pro Met Gly Tyr Gly Thr Leu
145                 150                 155                 160

Phe Pro Gly Tyr Gly Gly Phe Arg Gln Thr Leu Arg Gly Leu Asn Gln
                165                 170                 175

Asn Ser Pro Lys Gly Gly Asp Phe Thr Val Glu Val Asp Ser Pro Val
            180                 185                 190

Ser Val Thr Lys Gly Pro Glu Lys Gly Glu Gly Pro Glu Gly Ser Pro
        195                 200                 205

Leu Gln Glu Pro Ser Pro Asp Lys Gly Glu Asn Pro Ala Leu Leu Ser
    210                 215                 220

Gln Ile Ala Pro Gly Ala His Ala Gly Leu Leu Ala Phe Pro Asn Asp
225                 230                 235                 240

His Ile Pro Asn Met Ala Arg Gly Pro Ala Gly Gln Arg Leu Leu Gly
                245                 250                 255

Val Thr Pro Ala Ala Asp Pro Leu Ile Thr Pro Glu Leu Ala Glu
            260                 265                 270

Val Tyr Glu Thr Tyr Gly Ala Asp Val Thr Thr Pro Leu Gly Asp Gly
        275                 280                 285

Glu Ala Thr Met Asp Ile Thr Met Ser Pro Asp Thr Gln Gln Pro Pro
    290                 295                 300
```

-continued

```
Met Pro Gly Asn Lys Val His Gln Pro Gln Val His Asn Ala Trp Arg
305                 310                 315                 320

Phe Gln Glu Pro
```